United States Patent
Vogt et al.

[19]

[11] Patent Number: 6,132,409
[45] Date of Patent: *Oct. 17, 2000

[54] PERSONAL CARE ARTICLE WITH APERTURE ALIGNED FOR RECEIVING FECAL MATERIAL

[75] Inventors: Robert Eugene Vogt, Neenah; Paul John Serbiak, Appleton; Barbara Oakley Sauer, Fremont, all of Wis.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/862,458

[22] Filed: May 23, 1997

Related U.S. Application Data

[63] Continuation-in-part of application No. 08/705,374, Aug. 29, 1996, abandoned.

[51] Int. Cl.[7] ............................... A61F 5/44; A61F 13/15
[52] U.S. Cl. ................... 604/348; 604/355; 604/385.08; 604/385.19
[58] Field of Search ..................... 604/348, 355, 604/378, 385.1, 395, 393, 385.08, 385.19

[56] References Cited

U.S. PATENT DOCUMENTS

| | | |
|---|---|---|
| 3,192,926 | 7/1965 | Callaghan . |
| 3,424,160 | 1/1969 | Koornwinder et al. . |
| 3,532,093 | 10/1970 | Lovret . |
| 4,205,679 | 6/1980 | Repke et al. ............................. 128/287 |
| 4,892,536 | 1/1990 | DesMarais et al. .................. 604/385.2 |
| 4,950,262 | 8/1990 | Takagi .................................... 604/385.1 |
| 4,968,312 | 11/1990 | Khan ...................................... 604/388.1 |
| 4,990,147 | 2/1991 | Freeland ................................ 604/385.2 |
| 5,037,416 | 8/1991 | Allen et al. ........................... 604/385.1 |
| 5,062,840 | 11/1991 | Holt et al. .............................. 604/385.1 |
| 5,171,236 | 12/1992 | Dreier et al. ............................. 604/369 |
| 5,207,663 | 5/1993 | McQueen .............................. 604/385.1 |
| 5,269,775 | 12/1993 | Freeland et al. ...................... 604/385.2 |
| 5,624,422 | 4/1997 | Allen ..................................... 604/385.1 |

FOREIGN PATENT DOCUMENTS

| | | |
|---|---|---|
| 0357298 A2 | 3/1990 | European Pat. Off. . |
| 0359410 A1 | 3/1990 | European Pat. Off. . |
| 0626160 A1 | 11/1994 | European Pat. Off. . |
| 2 268 073 | 1/1994 | United Kingdom . |
| 2 284 537 | 6/1995 | United Kingdom . |
| 2284550 | 6/1995 | United Kingdom . |
| 2 289 419 | 11/1995 | United Kingdom . |
| 2294398 | 5/1996 | United Kingdom . |
| 2297474 | 8/1996 | United Kingdom . |
| 16418 | 6/1995 | WIPO ................................ 604/385.1 |
| WO 96/09026 | 3/1996 | WIPO . |
| 20674 | 7/1996 | WIPO ................................ 604/385.1 |
| WO 96/23465 | 8/1996 | WIPO . |
| WO 96/23466 | 8/1996 | WIPO . |
| WO 96/34588 | 11/1996 | WIPO . |

*Primary Examiner*—Mark O. Polutta
*Attorney, Agent, or Firm*—Thomas D. Wilhelm

[57] ABSTRACT

A personal care article for preventing exudates from contacting the body of a user comprises a substrate including an extensible bodyside liner layer, and an aperture support structure limiting extensibility of the bodyside liner layer along the length of the aperture support structure. One support band of an aperture support structure runs through the gluteal fold between the buttocks of a user. The aperture support structure positions an aperture in the bodyside liner layer in the gluteal fold of a user, in alignment with the anus, so that fecal material enters a containment receptacle upon leaving the anus. In another embodiment, the personal care article can include a comfort stretch layer comprising an elastomeric, hot melt, pressure-sensitive adhesive located between a bodyside liner layer and an outer layer. Elastomeric elements can follow the outside edges along the length of the personal care article and then curve inwardly at the crotch portion and cross each other at a cooperative location frontward of the aperture and corresponding to the perineum of a user. The personal care article can also have a first length at rest, and a second length when secured to the body of a user, the second length being at least 30% greater than the first length.

24 Claims, 10 Drawing Sheets

6,132,409

PERSONAL CARE ARTICLE WITH APERTURE ALIGNED FOR RECEIVING FECAL MATERIAL

CROSS-REFERENCE TO RELATED APPLICATIONS

This application is a continuation-in-part of application Ser. No. 08/705,374 filed Aug. 29, 1996, now abandoned.

This application claims priority under 35 U.S.C. 120 of application Ser. No. 08/705,374, filed Aug. 29, 1996, now abandoned.

FIELD OF THE INVENTION

Absorbent articles such as infant diapers, training pants, adult incontinence products, and the like are well known. Such articles have achieved a wide acceptance due to their ability to receive and absorb body exudates.

This invention pertains to a personal care article for containing body exudates. This invention utilizes an aperture mounted in the gluteal fold of a user to minimize contact of fecal material with the skin of a user. The aperture transfers fecal material to an exudate containment receptacle formed by an exudate panel mounted on the substrate.

BACKGROUND OF THE INVENTION

In general, body exudates of urine and fecal material should be received and contained by the absorbent article. However, leakage problems are common, especially of fecal material. Furthermore, even if exudates do not leak, they can have an adverse impact on the skin of a user of an absorbent article because of contact between exudates and the buttocks and other areas of the body within the absorbent article.

Conventional absorbent articles include a bodyside liner, an absorbent core, and an outer cover, made as a laminate composite and wrapped around the body of a user as a unified structure. To the extent known, holes in the bodyside liner have not been completely satisfactory to remove fecal material. The materials of the absorbent article, in combination, act to pull the bodyside liner away from the body of the user, forming a gap between the anus of the user and the bodyside liner. This gap allows fecal material to spread both lengthwise of the absorbent article and transversely, between the bodyside liner and the body of the user. Such spreading displaces the fecal material from alignment with any such holes in the bodyside liner. Thus, even if fecal material receiving holes exist in the bodyside liner of known absorbent articles, the fecal material is not efficiently and eptured through such hole and removed from contact with the skin of the user. At times, this gap even allows fecal material to leak from the absorbent article.

U.S. Pat. No. 5,207,663 discloses a urinary and bowel incontinency control undergarment having an elasticized double panel pouch that is suspended from a waistband. A rear elastic seam 36 assists in drawing the inner panel 16 of the pouch between the buttocks of the wearer. However, the elasticity of such structure precludes enhanced positioning of the aperture with respect to a specific body element of the user. An aperture 30 is surrounded by elastic material. No aperture supporting structure or other aperture positioning structure extends frontwardly from the aperture. A separate urinary pad, unrelated to the pouch formed in the rear of the absorbent article, is used to store urine.

U.S. Pat. No. 4,950,262 discloses a bellows type storage member which expands outwardly to store excretions. There is no disclosure of placing the aperture for the storage member in the gluteal fold between the buttocks of a user.

SUMMARY OF THE DISCLOSURE

In the present invention, a personal care article for receiving exudates isolates and minimizes contact of exudate material with the skin of the user through improved positioning of an aperture, in the bodyside liner, in the gluteal fold between the buttocks. This improved positioning prevents significant amounts of exudates from reaching or spreading on the buttocks, and from generally spreading between the bodyside liner and the skin of the user, and thus reaching other organs.

In one embodiment, the personal care article has a length and a width. The personal care article comprises a substrate, including an extensible bodyside liner, at least one aperture in the substrate positioned to receive fecal material, and aperture support structure effective to reduce extensibility of the substrate along the aperture support structure. The aperture support structure positions and seats the aperture in the gluteal fold between the buttocks of a user at or adjacent, and in alignment with, the anus, to receive fecal material.

In most embodiments, the personal care article includes an exudate panel secured to the substrate and defining an exudate containment receptacle between the exudate panel and the substrate. The exudate panel is positioned over the aperture such that the exudate containment receptacle receives exudates through the aperture. The exudate panel preferably has a second length substantially aligned with the first length of the personal care article. An indentation extends across the first length of the personal care article and inwardly toward the substrate at least about 30% of the thermoformed depth of the receptacle such that the effective second length of the exudate panel increases when the containment receptacle is bent or filled with exudates.

In some embodiments the exudate panel is secured over a second partial length of the substrate and defines an exudate containment receptacle between the exudate panel and the substrate. The aperture support structure can extend substantially the full amount of the second partial length of the substrate.

In some embodiments, undulations extend across the exudate panel such that the effective length of the exudate panel increases when the containment receptacle is bent or filled with exudates.

In another embodiment, the personal care article includes an exudate panel secured to the substrate and defining front and rear containment receptacles having depths between the exudate panel and the substrate. The exudate panel is positioned over at least one aperture such that the rear containment receptacle receives exudates through the aperture. The front and rear containment receptacles can be connected by at least one passageway to allow the transfer of exudates therebetween.

In some embodiments, the aperture support structure is extensible by about 5% from the length thereof at rest.

In most preferred embodiments, the bodyside liner comprises an elastomeric material extensible in both "x" and "y" directions. The bodyside liner has a stretch-to-stop extensibility from about 20% to about 200% of its length at rest in both directions. The bodyside liner generally is substantially impermeable to liquid.

In one embodiment, the aperture support structure comprises portions of the extensible bodyside liner treated with adhesives to thereby reduce extensibility.

In another embodiment, the aperture support structure comprises one or more separate pieces of material, the separate material being secured to the extensible bodyside liner.

In yet another embodiment, the aperture support structure comprises portions of the extensible bodyside liner treated with heat to thereby reduce extensibility.

In most preferred embodiments, the aperture support structure includes at least one support band. The support band extends between the aperture and preferably the front edge of the personal care article. The aperture support structure has a support band which positions and seats the aperture in the gluteal fold between the buttocks of a user at or adjacent, and in alignment with, the anus, to receive fecal material.

In preferred embodiments, a second support band of the aperture support structure extends between the aperture and preferably the front edge of the personal care article. The personal care article has a longitudinal axis extending between the front portion and the rear portion along the length of the personal care article. The longitudinal axis is centered across the width of the personal care article. The first and second support bands of the aperture support structure each form an angle of between about 10 degrees and about 40 degrees with respect to the longitudinal axis and corresponding angles with each other.

In preferred embodiments, the first and second support bands define a space therebetween, and include a liquid transfer structure in the space between the first and second support bands. The liquid transfer structure allows body exudate liquids to pass therethrough and into a containment receptacle.

In most preferred embodiments, a third support band of the aperture support structure extends between the aperture and preferably the rear edge of the personal care article.

In some embodiments, the aperture support structure effectively surrounds the aperture.

In some embodiments the aperture support structure extends the length of the personal care article.

In another embodiment, the personal care article has a substrate including an exudate panel. The substrate includes a bodyside liner. The bodyside liner includes an aperture. The exudate panel has a rear wall, and inwardly folded front edges defining a front wall. The front wall is secured to the substrate, thereby securing the exudate panel to the substrate and defining an exudate containment receptacle between the substrate and the exudate panel. The aperture opens into the exudate containment receptacle. At least part of the front wall of the exudate panel conforms to the substrate, and thus to the body of the user. The effective length of at least the rear wall increases in response to forces urging increase in length.

In some embodiments, the exudate panel has undulations extending across substantially the entire width, and disposed along substantially the entire length, of the exudate panel such that the rear wall of the panel is extensible. Peak-to-peak lengths of the undulations increase the effective length of at least the rear wall of the exudate panel in response to forces urging elongation of the rear wall.

The undulations can comprise creping formed in the exudate panel.

In some embodiments, the front wall of the exudate panel is open along a length thereof and, together with the rear wall, defines a rectangular shape to the exudate panel. The ends of the exudate panel can be crimped and secured to the substrate.

In some embodiments, the personal care article includes an outer cover secured to the substrate and over the exudate panel.

In most embodiments, the surface area defined within the aperture is at least about 2.4 square centimeters. The aperture defines an opening about 0.25 inch to about 0.38 inch wide and about 1.5 inches to about 2 inches long.

In another embodiment, the personal care article has a front portion and a rear portion, a substrate, including a bodyside liner, an aperture in the substrate positioned to receive fecal material and an aperture support structure positioning and seating the aperture in the gluteal fold between the buttocks of a user to receive fecal material. This embodiment includes a liquid transfer structure in the front portion of the personal care article which allows urine to pass therethrough. An exudate containment panel is secured to the substrate and defines in part an exudate containment receptacle. The exudate containment receptacle receives and contains fecal material passing through the aperture and urine passing through the liquid transfer structure.

In some embodiments, the liquid transfer structure comprises a portion of the bodyside liner treated with surfactant to enable urine to pass therethrough.

In some embodiments, the exudate containment receptacle includes superabsorbent material to receive and retain liquid. The exudate containment receptacle preferably has a capacity of between about 300 milliliters and about 500 milliliters. The exudate containment receptacle has a slippery inner surface such that exudates flow easily throughout the containment receptacle.

In most embodiments, the personal care article is free from containment flaps and leg cuffs.

In another family of embodiments, the personal care article has a length and a width, the personal care article comprises a substrate, including (i) an inner bodyside liner layer, (ii) an outer layer, and (iii) a comfort stretch layer between the inner bodyside liner and the outer layer; at least one aperture in the substrate; and aperture support structure secured to the substrate, the aperture support structure positioning and seating the at least one aperture in the gluteal fold between the buttocks of a user at or adjacent, and in alignment with, the anus, to receive fecal material from the anus, the comfort stretch layer assisting in the substrate maintaining effective contact with the body of the user.

In most embodiments, the substrate including the comfort stretch layer can be extensible in both "x" and "y" directions. The comfort stretch layer can have a maximum stretch-to-stop extensibility in both the "x" and "y" directions of at least 300% of the length at rest. A first side of the comfort stretch layer is in surface-to-surface relationship with the inner bodyside liner layer. A second opposing side of the comfort stretch layer is in surface-to-surface relationship with the outer layer. The comfort stretch layer can be secured to the inner bodyside liner layer and the outer layer such that full extended dimensions of at least one of the inner bodyside liner layer and the outer layer represent a stretched dimension of the comfort stretch layer. The portion of the personal care article which includes the comfort stretch layer therein thereby has greater extensibility from a rest condition than portions of the personal care article which do not include the comfort stretch layer therein. The comfort stretch layer can comprise a stress/strain relationship of 0.75 grams per 1.0% elongation per inch width. The comfort stretch layer can be symmetric about longitudinal axis.

In some embodiments, the comfort stretch layer can have a width about one-third as great as the width of the personal care article. In other embodiments, the comfort stretch layer can have a width approximating the width of the personal care article.

In some embodiments, the aperture support structure can be located between the inner bodyside liner layer and the outer layer.

In some embodiments, the aperture support structure comprises first and second support bands extending from the rear portion frontwardly along respective first and second spaced paths, the first and second support bands extending inwardly toward each other at the crotch portion of the personal care article, and effectively meeting one another at a cooperative location proximate the perineum of the body of a user, the support bands assisting in positioning and seating the at least one aperture in the gluteal fold between the buttocks of the user at or adjacent, and in alignment with, the anus, to receive fecal material from the anus.

The spaced paths of the first and second support bands preferably extend substantially along first and second opposing outside edges in the rear portion of the personal care article.

In some embodiments, the first and second support bands, after effectively meeting at a cooperative location, cross each other and extend therefrom in outwardly and frontwardly disposed curves, toward the front edge of the front portion of the personal care article. The first and second support bands can extend along respective second and first opposing outside edges in the front portion of the personal care article.

In some embodiments, a third support band effectively extends about the perimeter of the at least one aperture and extends substantially along the longitudinal axis to the rear edge of the personal care article. Thus the third support band assists in positioning and seating the at least one aperture in the gluteal fold between the buttocks of a user at or adjacent, and in alignment with, the anus, to receive fecal material from the anus.

In some embodiments, the support bands comprise a multiplicity of elastomeric elements, the elastomeric elements being stretched when secured to the substrate.

In most embodiments, the first and second support bands have less strain elongation per unit of stressing force than the comfort stretch layer.

In some embodiments, the substrate includes a multiplicity of apertures therethrough in the front portion of the personal care article to allow body exudate liquid to pass therethrough.

In some embodiments, the bodyside liner layer, the outer layer, and the comfort stretch layer have a first elongation per unit of force applied thereto greater than a second elongation per unit of force applied to the aperture support structure.

In most embodiments, the comfort stretch layer comprises an elastomeric, hot melt adhesive. The comfort stretch layer can comprise an elastomeric, pressure-sensitive adhesive.

In another family of embodiments, the personal care article has a front portion and a front edge, a crotch portion, a rear portion and a rear edge, a length and a width, the personal care article comprising: a substrate, including an extensible bodyside liner layer; at least one aperture in the substrate; and aperture support structure secured to the substrate and comprising first and second bands meeting one another at a cooperative location along a central axis in the crotch portion, frontwardly of the aperture, the cooperative location being proximate the perineum of the body of a user, the aperture support structure assisting in positioning and seating the at least one aperture in the gluteal fold between the buttocks of the user at or adjacent, and in alignment with, the anus, to receive fecal material from the anus.

In most embodiments, the extensible bodyside liner layer has a first elongation per unit of force applied thereto greater than a second elongation per unit of force applied to the aperture support structure.

In another family of embodiments, the personal care article has a front portion and a front edge, a crotch portion, a rear portion and a rear edge, a length and a width, a longitudinal axis extending through the front portion, crotch portion, and rear portion, the personal care article comprising a substrate, including a comfort stretch layer, the substrate being extensible at least along the longitudinal axis, the personal care article having a first length between the front edge and the rear edge when the personal care article is relaxed, the personal care article having a second length between the front edge and the rear edge when stretched an amount required for application to the body of a user, the second length being at least 30% greater than the first length. The second length can be at least 40%, 50%, 60%, 70%, 80% or 90% greater than the first length, depending on the design of the personal care article.

In most embodiments, the comfort stretch layer comprises a unitary sheet of material. The unitary sheet preferably has a thickness of about 0.001 inch to about 0.05 inch.

BRIEF DESCRIPTION OF THE DRAWINGS

FIG. 7 shows a cross section of the exudate panel of the embodiment of FIG. 5.

Figures 2A, 2B:
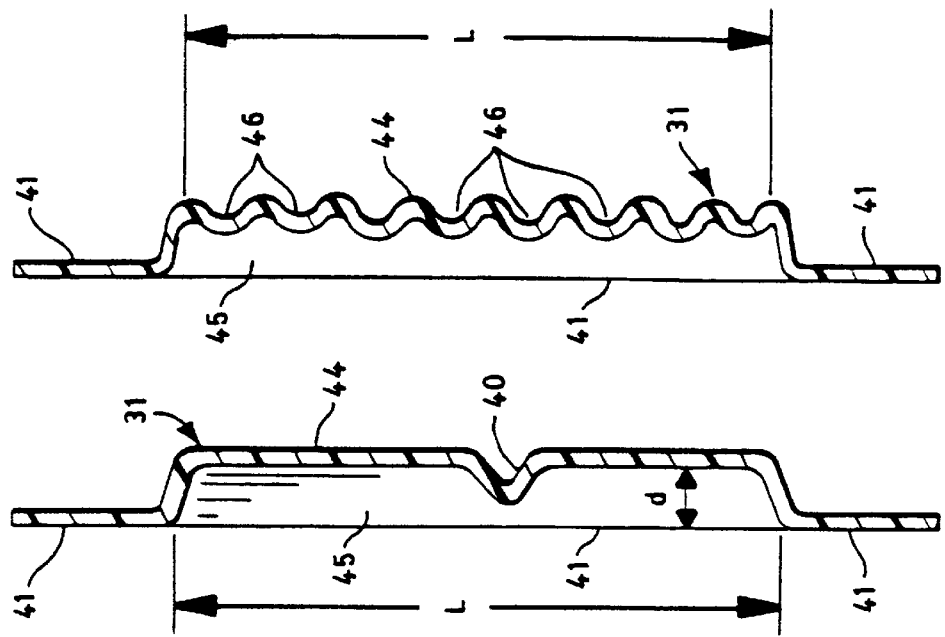
FIG. 2A shows a cross section of a first exudate panel of the personal care article of FIG. 1.
FIG. 2B shows a cross section of a second embodiment of an exudate panel of the personal care article of FIG. 1.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. The drawings are for purposes of illustration, and are not necessarily drawn to scale.

DETAILED DESCRIPTION OF THE ILLUSTRATED EMBODIMENTS

Figure 1:
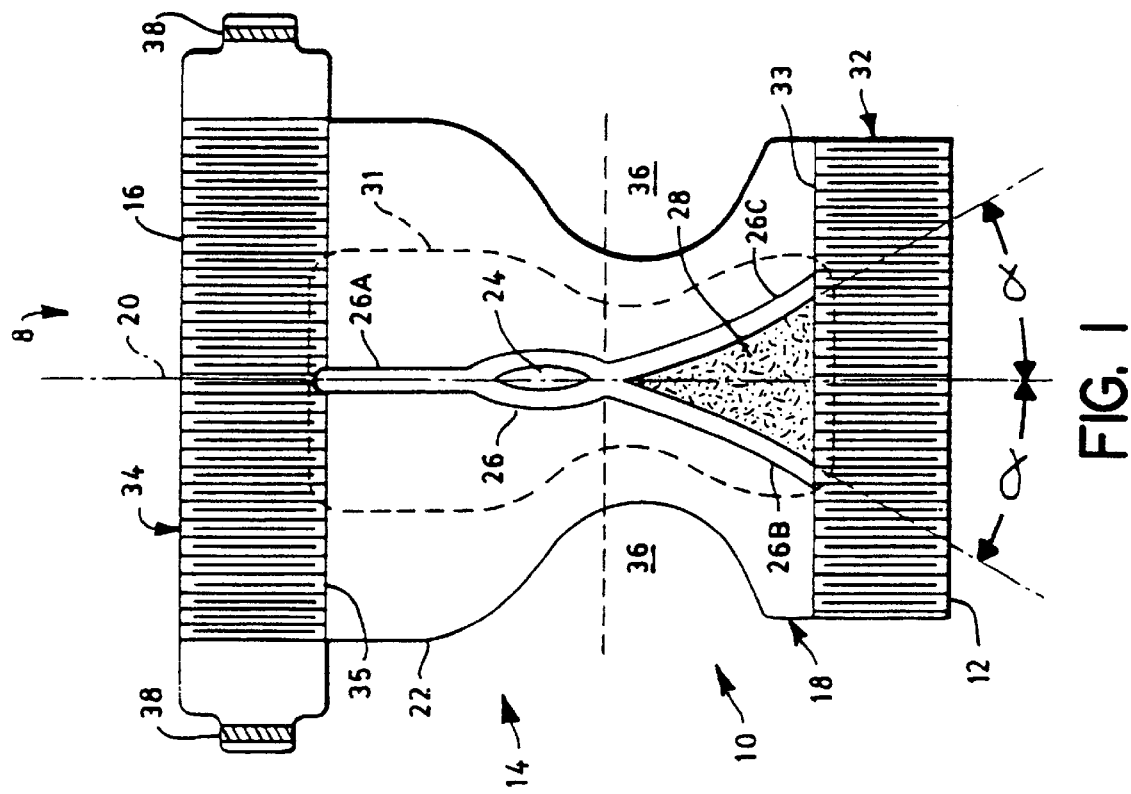
FIG. 1 shows a top view of a first embodiment of personal care articles of the invention.
Figure 4:
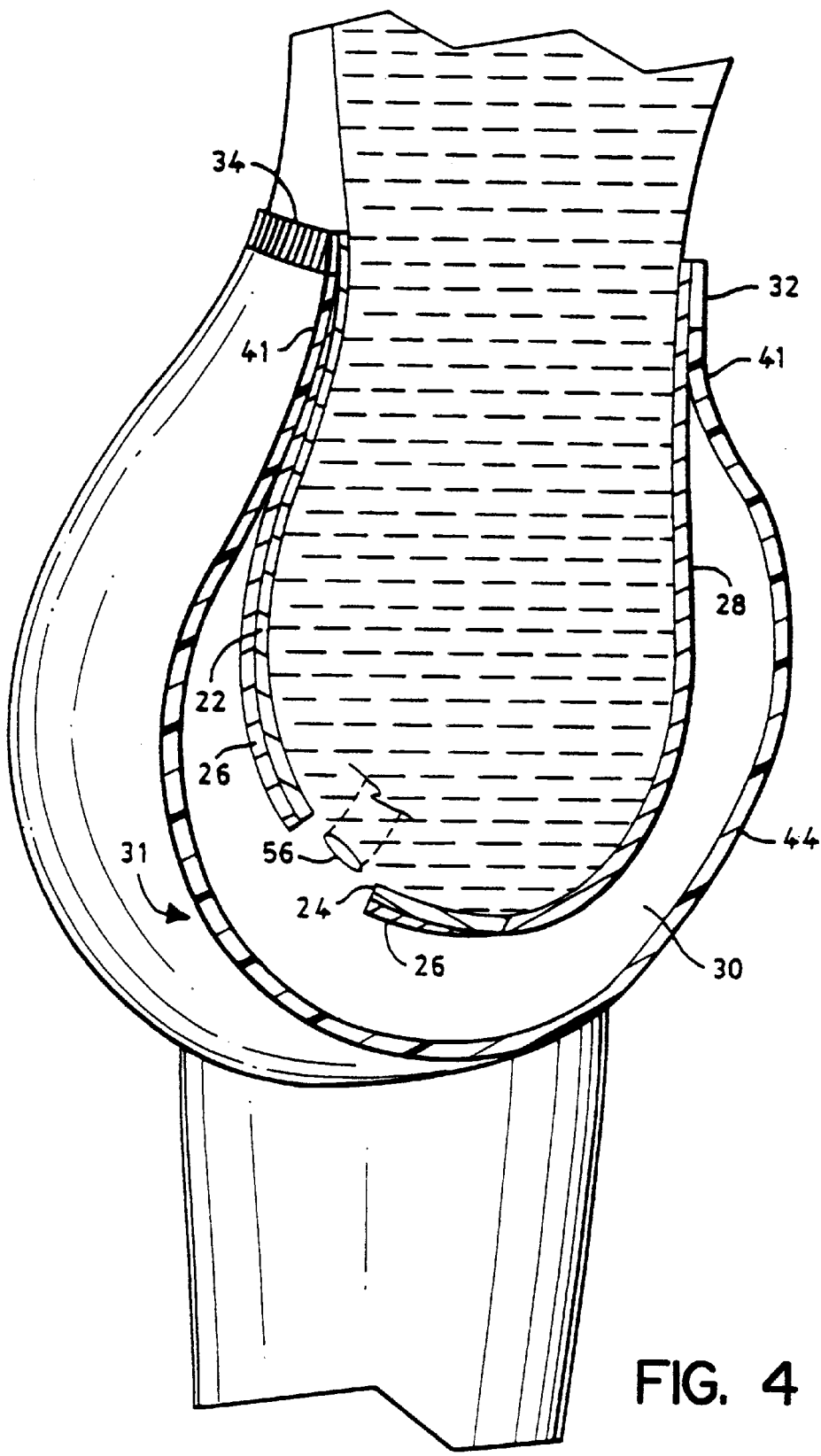
FIG. 4 shows a cross-section view of the personal care article taken at 4—4 of FIG. 3.

The personal care article 8 shown in FIG. 1 includes a front portion 10 having a front edge 12, a rear portion 14 having a rear edge 16. A longitudinal axis 20, centered across the width of personal care article 8, extends through front portion 10 and rear portion 14. Personal care article 8 includes a substrate 18 having a bodyside liner 22, an aperture 24, and aperture support structure 26 supporting the aperture. Aperture 24 allows fecal material to pass through bodyside liner 22 and liquid transfer structure 28 allows urine to pass through bodyside liner 22, both to exudate containment receptacle 30 (FIG. 4). Exudate containment receptacle 30 is defined in general by substrate 18 and exudate panel 31. Front waistband 32, rear waistband 34, and leg cut-outs 36 enhance mounting of personal care article 8 using fasteners 38 or the like and an attachment surface (not shown) secured to front portion 10 of the personal care article. In the embodiment of FIG. 2A, exudate panel 31 includes an indentation 40. Flange 41 of exudate panel 31 is secured to bodyside liner 22. Indentation 40 allows expansion of rear wall 44 when personal care article 8 is bent as it is mounted on a user.

Bodyside liner 22 preferably comprises a material having a stretch-to-stop extensibility in both the "x" and "y" directions, from about 20% to about 200% of its length at rest. The "x" and "y" directions represent the width direction and the length direction, respectively, of bodyside liner 22. The length direction corresponds to the direction of longitudinal axis 20. Bodyside liner 22 is preferably impermeable to body exudate liquids, although in some embodiments, some or all of the bodyside liner may be permeable to body exudate liquids. In embodiments where bodyside liner 22 is impermeable to liquids, the bodyside liner can permit the passage of air or other gases therethrough.

In one embodiment of the present invention, bodyside liner 22 can comprise a stretch-bonded laminate having appropriate elasticity and width to create a surface contact with the body of a user. A stretch-bonded laminate comprises at least a two layered composite in which one layer is a gatherable layer and the other layer a stretchable layer. The layers are joined together when the stretchable layer is in a stretched condition so that, upon relaxing the layers, the gatherable layer is gathered. The stretchable layer can be a film of stretchable material, such as a layer of styrene ethylene butylene styrene or other elastomeric polymer, or a plurality of strands of a stretchable material such as latex. Other materials with similar properties may also be provided integral with or attached to bodyside liner 22. Such materials should not interfere with the soft texture of bodyside liner 22 against the skin of a user.

Examples of materials suitable for bodyside liner 22 include a wide selection of web materials, such as foams, plastic films or natural or synthetic fibers. Other possible materials are webs made from synthetic fibers, such as polyester or polypropylene fibers, or a combination of natural and synthetic fibers. For example, neckbonded spunbond material can be used for bodyside liner 22. Part of bodyside liner 22 within the outline of exudate panel 31 shown in FIG. 1 is suitably utilized to help isolate the liquids held in exudate containment receptacle 30. Bodyside liner 22 may be composed of a substantially hydrophobic material. The materials must be necked or creped or otherwise formed to provide extensibility in at least one direction. Further, bodyside liner 22 may optionally be composed of a micro-porous material which permits vapors to escape through bodyside liner while preventing liquid exudates from passing through.

In another embodiment of the present invention, bodyside liner 22 may comprise a spunbonded polypropylene fabric composed of about 2.8–3.2 denier fibers formed into a web having a basis weight of about 22 grams per square meter and a density of about 0.06 grams per cubic centimeter which has been creped or necked such that it is extensible in at least one of the "x" and "y" directions. Bodyside liner 22 may comprise a multiplicity of components, layers, or partial layers, which correspond to any of the materials disclosed herein, as well as others known in the art.

Substrate 18 includes bodyside liner 22, and can include other elements, such as aperture support structure 26, front waistband 32, rear waistband 34, fasteners 38 or the like. Substrate 18 can include additional layers or partial layers. Substrate 18 can include outer cover 50 (FIG. 8B), at least in regions where outer cover 50 is secured to bodyside liner 22.

Aperture 24 extends through and is preferably cut out or otherwise formed in, bodyside liner 22. With bodyside liner 22 laid out flat at rest, aperture 24 preferably encompasses within its outer perimeter a surface area of at least about 2.4 square centimeters. A preferred shape for aperture 24 comprises a slot about 0.25 inch to about 0.38 inch wide and about 1.5 inches to about 2 inches in length. For example, aperture 24 may vary in length and width, preferably having a length-to-width ratio of from between about 4:1 for a relatively wide aperture and a length-to-width ratio of about 10:1 for a longer aperture. The length direction of aperture 24 corresponds to the length of personal care article 8 along longitudinal axis 20. Other aperture shapes, such as rectangular, slit, oval or elliptical, can also be used effectively. A slit can have a V-cut or X-cut type shape such that tension causes lines of force that open the slit.

Aperture support structure 26 surrounds aperture 24 as shown in FIG. 1. A variety of mechanisms can be used to create aperture support structure 26. For example, aperture support structure 26 can be created by adhesively treating portions of bodyside liner 22 at selected locations, for example the locations shown. The adhesive reduces the elasticity of bodyside liner 22 and thus prevents or decreases expansibility of the bodyside liner along and adjacent the adhesively treated portions.

In a second family of embodiments, aperture support structure 26 is created by heat treating portions of bodyside liner 22. Heat treating reduces the elasticity of bodyside liner 22 in the treated region and thus prevents or decreases extensibility of the bodyside liner along and adjacent the heat treated portions. Application of ultrasonic energy, such as ultrasonic bonding is one method of reducing the elasticity by such heat treatment.

In a third family of embodiments, aperture support structure 26 comprises cords of spandex material having expansibility moduli higher than respective expansibility moduli of bodyside liner 22, secured preferably to the outer surface of the bodyside liner, away from the body of the user. Other possible materials include twisted cord such as thread, yarn or any other elongate material secured to bodyside liner 22, which limits longitudinal expansibility of substrate 18 along aperture support structure 26. Aperture support structure 26 can be secured to the inner surface of bodyside liner 22. However, in such instances, the material of aperture support structure 26 should be soft and comfortable for contacting the body of the user. When aperture support structure 26 comprises separate e.g. elongate elements in addition to bodyside liner 22, the separate elements can be glued, thermally bonded, sewn or otherwise secured to substrate 18. Other methods well known to one of ordinary skill in the art can be utilized to form aperture support structure 26.

However aperture support structure 26 is formed, the aperture support structure is less extensible than the portion of the bodyside liner to which it is applied. Preferred stretch-to-stop extensibility for aperture support structure 26 is from about 1% to about 10% of its length at rest, and most preferably about 5%, compared to, for example, about 20% to about 200% extensibility for bodyside liner 22.

Figure 5:
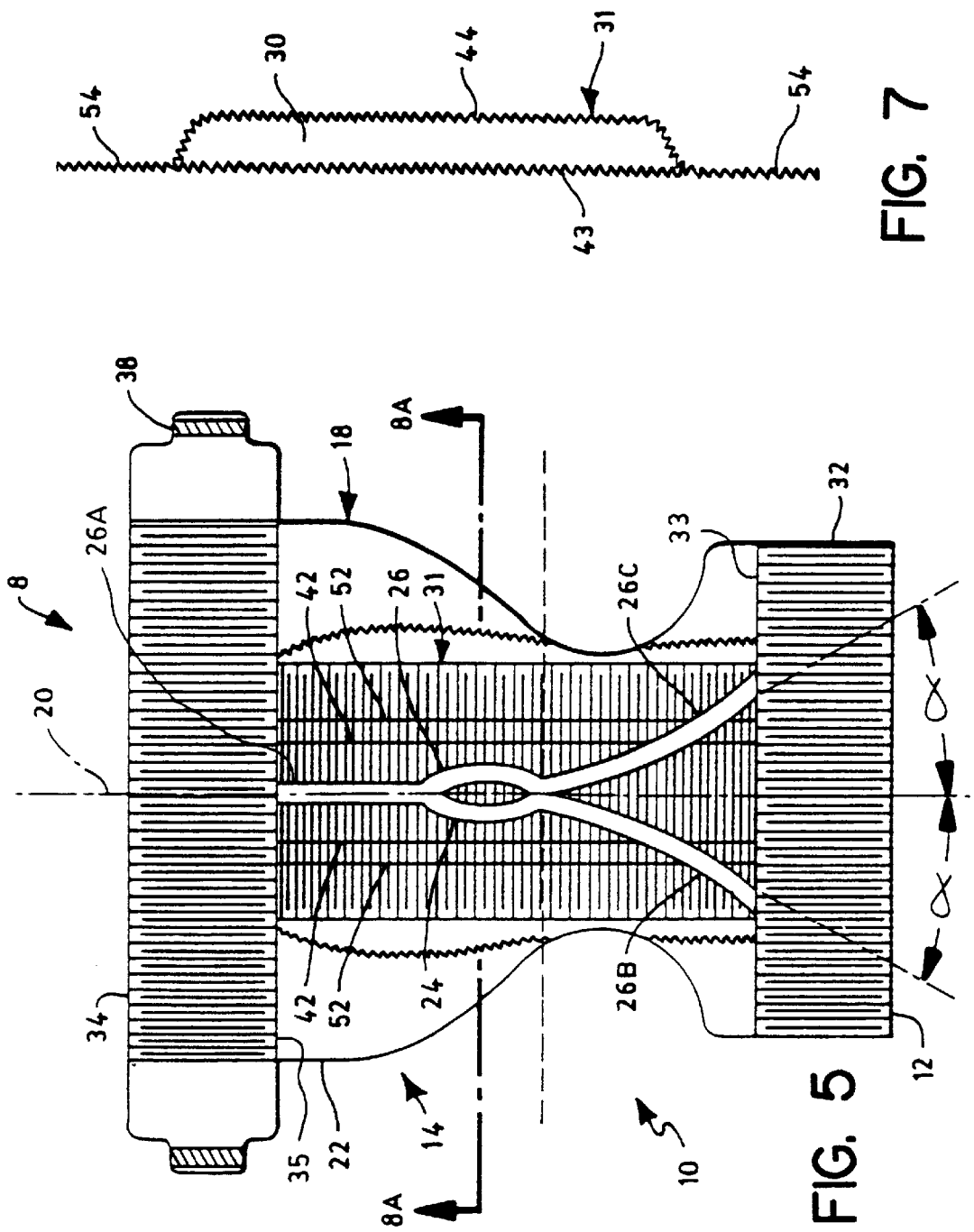
FIG. 5 shows a top view of a second embodiment of personal care articles of the invention having center portions of the bodyside liner cut-away.

Aperture support structure 26 generally surrounds aperture 24. In one embodiment, a rear support band 26A of the aperture support structure generally extends from the aperture substantially along longitudinal axis 20 toward rear edge 16 of personal care article 8 as shown in FIGS. 1 and 5. Rear support band 26A can extend to rear edge 16 or can terminate closer to e.g. the inward side 35 of rear waistband 34.

Two front support bands 26B, 26C of aperture support structure 26 may extend from aperture 24 frontwardly toward front edge 12 of personal care article 8. These two support bands 26B, 26C can extend to front edge 12 or can terminate closer to e.g. the inward side 33 of front waistband 32. Each of support bands 26B, 26C forms an angled α of between about 10 and about 40 degrees with respect to longitudinal axis 20.

Optionally, a support band (not shown) may span aperture 24 in order to assist in maintaining the aperture in an open position. In a preferred option, the support band (not shown) follows the direction of longitudinal axis 20 through the center of aperture 24. Such an arrangement may be considered as creating two apertures.

While support bands 26A, 26B, 26C are shown as continuous, discontinuities are contemplated. Similarly, a variety of lengths are contemplated for each of support bands 26A, 26B, 26C. The longer the support bands, and the less the collective effective lengths of any discontinuities, generally the more effective is aperture support structure 26 in positioning aperture 24 in alignment with the anus of the user. By contrast, the shorter the support banding and the greater the effective lengths of any discontinuities, generally the less effective is aperture support structure 26 in positioning the aperture in alignment with the anus of the user.

Liquid transfer structure 28 of personal care article 8 can comprise a liquid permeable region that allows urine to pass therethrough. Liquid transfer structure 28 can be formed by a portion of bodyside liner 22 which has been treated with surfactant or otherwise processed to impart a desired level of hydrophilicity and wettability. One suitable surfactant is TRITON X-102 available from Union Carbide, a business having offices in Danbury, Conn. The surfactant can be applied by any conventional means, such as spraying, printing, brush coating or the like.

Instead of being part of, or an extension of, or a material like that of bodyside liner 22, liquid transfer structure 28 can comprise a separate and different sheet material such as screen, mesh, apertured film, woven or non-woven material or the like, secured to substrate 18, and preferably secured to aperture support structure 26 and/or bodyside liner 22 of substrate 18. Liquid transfer structure 28 preferably allows passage of liquids in only one direction. The material of liquid transfer structure 28 preferably has a soft clothlike feel for contacting the body of the user.

Exudate panel 31 preferably has an hourglass shape as outlined in FIG. 1. Flange 41 of exudate panel 31 can follow the hourglass shape. Flange 41 preferably extends outwardly about the entire circumference of exudate panel 31. In FIGS. 2A and 2B, flange 41 is most visible on the top and bottom ends. While flange 41 is shown extending outwardly about the circumference of exudate panel 31, flange 41 can also extend inwardly about part or all of the circumference of the exudate panel.

Exudate panel 31 is preferably a thermoformed flexible material such as polypropylene, polyethylene, vinyl or the like. Alternatively, exudate panel 31 can comprise a liquid impermeable non-woven or woven material that has been creped. Exudate panel 31 has a rear wall 44 including an indentation 40, and side walls 45 as shown in FIG. 2A. Indentation 40 preferably crosses the full width of exudate panel 31. When exudate panel 31 is bent, as when personal care article 8 is installed on a user, indentation 40 decreases in depth, thereby increasing the effective length "L" of rear wall 44. While FIG. 2A shows indentation 40 substantially centered along the length of exudate panel 31, the indentation can be located toward the top or bottom areas of the panel as desired. Similarly, a multiplicity of such indentations can be used as desirable.

FIG. 2B shows a further extension of the concept of multiple indentations wherein regular undulations 46 extend the full length "L" of exudate panel 31. These undulations formed in the thermoplastic material allow further expansion of rear wall 44 of exudate panel 31. While FIG. 2B shows undulations 46 having a regular wavelike pattern, the pattern can be irregular. For example, the peak-to-peak distances between undulations 46 and the amplitudes of the undulations can vary. The undulations preferably extend across the entire length of exudate panel 31, but undulations 46 can also extend across only a portion of rear wall 44. Undulations 46 are but general examples of multiple indentations 40.

Exudate containment receptacle 30 has a thermoformed depth "d" as shown in FIG. 2A preferably from about ⅜ inch to about ½ inch. Indentation 40 preferably extends inwardly at least about 30%, and most preferably from about 30% to about 50% of the thermoformed depth "d" of containment receptacle 30. Exudate containment receptacle 30 preferably has a capacity to receive and hold about 300 milliliters to about 500 milliliters of exudates, and preferably about 350 milliliters.

In general, indentations 40 and undulations 46 extend only transverse to the length "L" of exudate panel 31. Thus, in preferred embodiments, and where the undulations or indentations extend inwardly between the preferred depth "d" of about 30% to about 50% for exudate panel 31, the undulations or indentations do not extend longitudinally along the length of exudate panel 31. Thus, indentation 40 and undulations 46 do not generally participate in enabling a significant increase in depth "d" when fecal material is received in containment receptacle 30. However, to the extent the indentations and/or undulations extend inwardly at least about 30% of depth "d", and preferably from about 30% to about 50% of depth "d", one or more generally longitudinally aligned indentations or undulations may be indicated in the invention.

Without limitation, exudate panel 31 typically has a thickness of about 0.5 mil to about 3 mils, and preferably about 2 mils. Exudate panel 31 is impermeable to liquids passing therethrough.

Exudate panel 31 generally is secured to the outer surface of bodyside liner 22 along flange 41 by adhesive or the like. Flange 41 has a sufficient width to secure exudate panel 31 to substrate 18, including securement against leakage of fluids from receptacle 30 about flange 31. Adhesive preferably secures flange 41 to substrate 18 such that neither the flange nor the substrate, including bodyside liner 22, can expand appreciably at the region of contact. The length of exudate panel 31 is generally aligned with the length of personal care article 8 as shown in FIGS. 1 and 5.

Exudate containment receptacle 30 is typically formed by the combination of bodyside liner 22 of substrate 18, and exudate panel 31. As seen in FIGS. 1, 2A, 2B, and 2C, exudate panel 31 comprises the outer wall, and the side walls, of exudate containment receptacle 30, and substrate 18 comprises the inner wall of the containment receptacle. Exudate panel 31 is positioned over aperture 24 so that exudate containment receptacle 30 receives exudates therethrough. Both bodyside liner 22 and exudate panel 31 are generally impermeable to liquids. The primary exception is front portion 10 at the liquid transfer structure 28 where bodyside liner 22 is typically treated to allow urine to pass through bodyside liner 22 into exudate containment receptacle 30. To that end, liquid transfer structure 28 can comprise a separate element, which may utilize a material different from the material used for bodyside liner 22.

Fasteners 38 can comprise a mechanical fastener such as the hooks of a hook and loop fastening system. An attachment surface (not shown) then comprises a corresponding loop material in front portion 10, adapted to releasably engage with the hook material to hold personal care article 8 on the body of the user. Other well known fastening apparatus can also be used to support personal care article 8 on the user. For example, a cohesive system, an adhesive fastener system, belt, or the like may also be utilized to support personal care article 8 on the user.

Fasteners 38 can be secured to bodyside liner 22, outer cover 50, or a location therebetween. Securement of fasteners 38 can be by adhesives, ultrasonic bonding or any other well known method.

Front waist band 32 and rear waistband 34 generally comprise elastics, such as strands, ribbons or one or more layers of a polymeric and/or elastomeric material which can be adhered in personal care article 8 while in a stretched condition. Front waist band 32 and rear waistband 34 can comprise one or more individual strands of elastomeric material, preferably in a spatially separated, generally parallel arrangement. Waistbands 32, 34 preferably are adhesively secured to bodyside liner 22.

While FIG. 1 shows waistbands 32, 34 secured to the inner surface of bodyside liner 22, the waistbands can be secured to the outer surface of the bodyside liner instead. Furthermore, waistbands 32, 34 can be secured to outer cover 50, or at least in part to exudate panel 31. The placement of waistbands 32, 34 with respect to the layer or layers forming substrate 18 is not critical.

Figure 3:
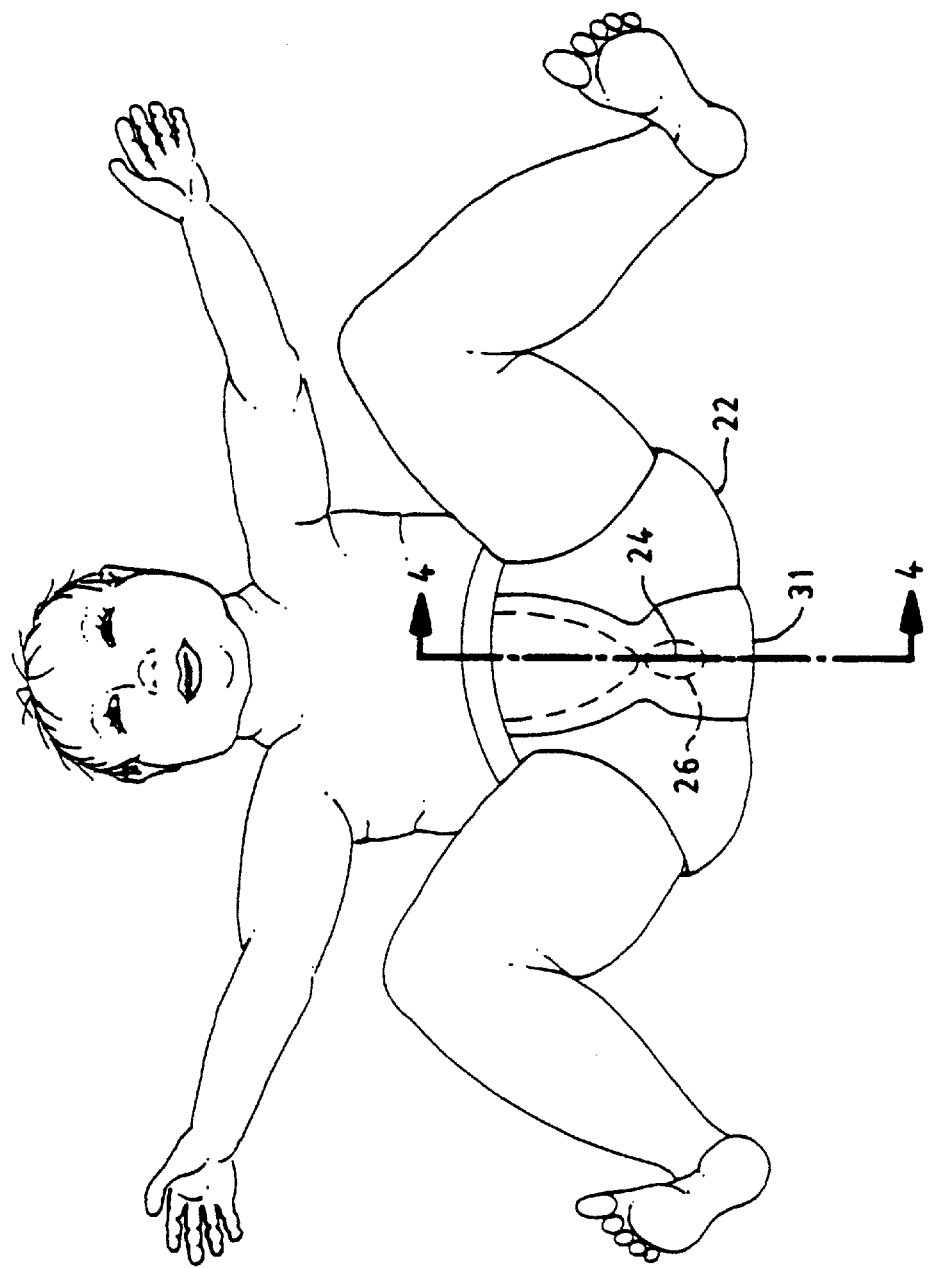
FIG. 3 shows the personal care article of FIG. 1 applied to the body of a user.

FIG. 3 shows personal care article 8 applied to the body of a user who is lying down. FIG. 4 shows a cross-section view of FIG. 3 depicting the relationship between exudate panel 31, bodyside liner 22, aperture 24 and anus 56 of the user. In this illustrated embodiment, aperture support structure 26 extends the length of personal care article 8, and thus assuredly positions aperture 24 at or adjacent, and in alignment with, anus 56. Exudate containment receptacle 30 preferably extends about both the front and back of the body of a user to collect both liquid exudates and fecal material. Exudate panel 31, having expandable rear wall 44, and in combination with bodyside liner 22, forms exudate containment receptacle 30.

FIG. 4 illustrates personal care article 8 bent as anticipated for mounting on a user. Accordingly, any gentle indentation 40 or undulations 46 have been absorbed by the general expansion of the length "L" of exudate panel 31, and are thus not visible in the depiction of FIG. 4. The embodiment of FIG. 4 does not show an outer cover 50. In operation, personal care article 8 of FIG. 1 is applied to the body of a user by bending the personal care article and securing fasteners 38 to a corresponding outer surface of front portion 10 to thus mount the personal care article on the user. Aperture support structure 26 surrounding aperture 24, shown by dashed lines in FIG. 3, and extending frontwardly and rearwardly from aperture 24, assists in maintaining the size and shape of the aperture despite the presence of diverse forces urging otherwise when the personal care article is in use. In this illustrated embodiment, rear support band 26A of aperture support structure 26 extends rearwardly toward rear waistband 34 along longitudinal axis 20. Such a rear support band 26A, when applied to the body of the user, resides in the gluteal fold between the buttocks. Thus rear support band 26A positions and seats aperture 24 in the gluteal fold between the buttocks of the user generally along the innermost line of skin in the gluteal fold, to receive fecal material. Aperture support structure 26 also may extend frontwardly from aperture 24 toward front edge 12 and assists in properly supporting the aperture adjacent the anus 56 of the user, from front portion 10 of personal care article 8. In the illustrated embodiment, front support bands 26B, 26C extend frontwardly from aperture 24, each at angle α respectively with respect to longitudinal axis 20 as shown in FIG. 1. In combination with rear support band 26A, front support bands 26B, 26C position or seat aperture 24 at or adjacent, and in alignment with, anus 56 of the user as shown in FIG. 4. By extending support bands 26B, 26C at angle a outwardly in the frontward direction, aperture support structure 26 avoids significantly interfering with the comfort of, or injuring the organs of the user. Further, the angles α of support bands 26B, 26C provide transverse support at aperture 24, resisting transverse movement of aperture 24 out of its central location in the gluteal fold. Thus personal care article 8 will receive and retain significant amounts of fecal material directly from anus 56 without the fecal material contacting the skin of the user at areas away from the anus.

Substrate 18, including bodyside liner 22 about exudate panel 31, can generally expand greatly for tight securement of personal care article 8 to the body of the user. Substrate 18, including bodyside liner 22 within the outline of exudate panel 31 (FIG. 1) can expand inwardly toward, and following the contours of, the body of the user in response to aperture support structure 26 seating aperture 24 adjacent anus 56 of the user.

Inward bending of personal care article 8 and corresponding placement of the personal care article on the body of the user also bends exudate panel 31. Instead of the bend greatly reducing the volume capacity by collapsing exudate panel 31 of exudate containment receptacle 30, indentation 40 shown in FIG. 2A (or undulations 46 of FIG. 2B) allows rear wall 44 to effectively lengthen and thus retain much of the volume capacity exhibited in the thermoformed position shown in FIGS. 2A, 2B. During normal usage, when a user sits down, containment receptacle 30 will collapse to the extent it conforms to the body of the user where pressure is applied. However, since aperture 24 is in physical contact with, or in close proximity to the anus of the user, there remains a substantial volume, between the buttocks, for exudates to enter and move about in, exudate containment receptacle 30. Further, areas of containment receptacle 30 not under pressure can expand to receive and retain exudates.

When exudates enter exudate containment receptacle 30, where and if not already in contact with the skin, areas of bodyside liner 22 within the outline of containment panel 31 can expand inwardly against the body of the user to create more storage space. More importantly, areas of containment panel 31 that are partially collapsed can also move outwardly to provide more volume. Rear wall 44 effectively lengthens, as described earlier, allowing for storage of exudates.

Exudate containment receptacle 30 desirably has a slippery inner surface that allows exudates to enter and flow easily throughout. Accordingly, as body forces are exerted on containment receptacle 30 from differing directions, exudates already in the receptacle easily move about the receptacle as the receptacle dynamically changes shape in response to such forces.

Optionally, exudate containment receptacle 30 can include superabsorbent material, for example, loosely contained within, or secured to the walls forming the containment receptacle. Such superabsorbent material can absorb urine passing through liquid transfer structure 28 and into containment receptacle 30 and liquids from fecal material. In use, containment receptacle 30 can receive and retain both fecal material via aperture 24 and urine via liquid transfer structure 28.

In operation, the embodiment of FIG. 2B works like the embodiment of FIG. 2A. Undulations 46 of containment receptacle 30 straighten and increase the effective length of rear wall 44. Undulations 46 extend across the entire width of rear wall 44 and can also include at least part of the side walls 45 of exudate panel 31.

Figure 2C:
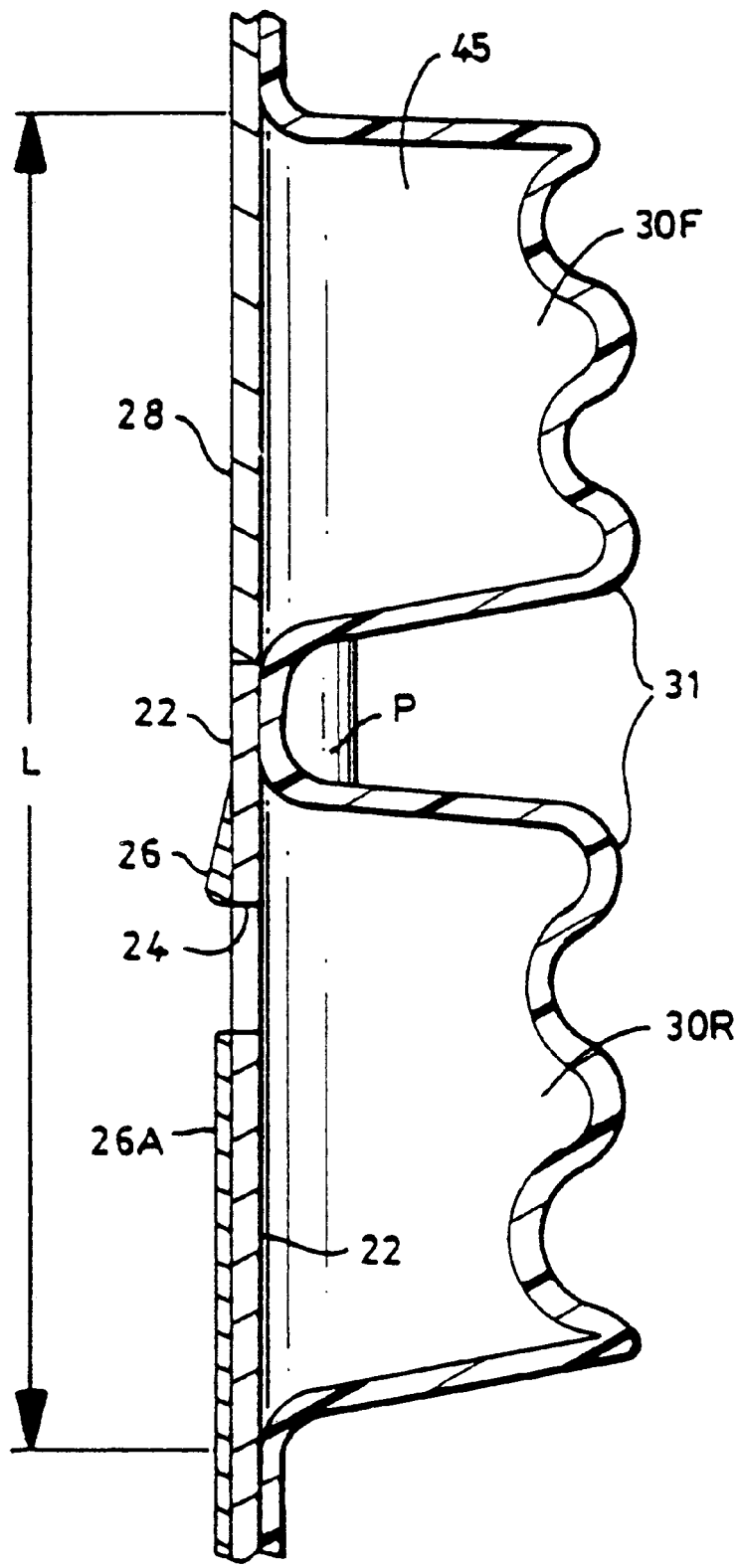
FIG. 2C shows a cross-section view of a third embodiment of a containment receptacle of the personal care article.

Another embodiment of the invention is contemplated where personal care article 8 can contain first and second front and rear containment receptacles 30F, 30R as shown in FIG. 2C. Front receptacle 30F receives urine-type exudates. Rear receptacle 30R receives fecal exudates. Such front and rear containment receptacles 30F, 30R have respective different exudate retention properties adapted to maximize retention and control of the respective exudates to be received. One or more optional communications passages "P" between the front and rear receptacles 30F, 30R provide for overflow of exudates from either such receptacle to the other, to thus provide overflow or back-up capacity. Optionally, front containment receptacle 30F can include superabsorbent material, for example, loosely contained within, or secured to the walls forming the containment receptacle. Rear containment receptacle 30R can also include superabsorbent material. While FIG. 2C shows a single exudate panel 31 centrally bonded to bodyside liner 22 of the substrate adjacent a passage "P" and assisting in forming containment receptacles 30F, 30R, multiple exudate panels can also be utilized.

Figure 6:
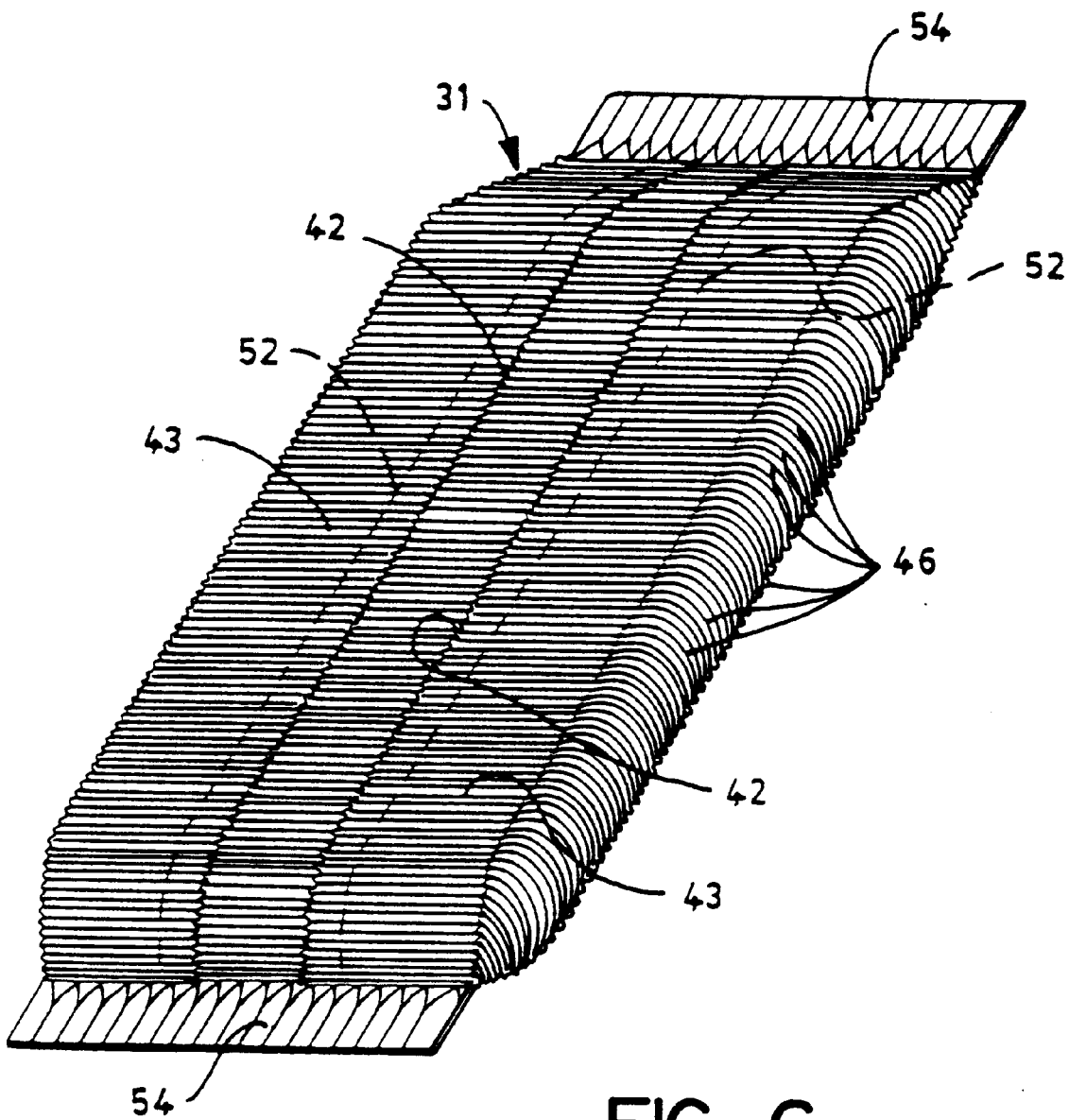
FIG. 6 shows an angled top view of the exudate panel of FIG. 5.

FIGS. 5 and 6 show a second embodiment of an exudate panel 31. The cutaway view of a central portion of the drawing shows personal care article 8 without bodyside liner 22. Aperture support structure 26 comprising an elongate material separate from bodyside liner 22 remains in FIG. 5 to show the relationship between aperture 24 and exudate panel 31. Other than exudate panel 31, the elements in FIG. 3 are the same as the corresponding elements shown in FIG. 5. While aperture support structure 26, including support bands 26A, 26B, 26C, is shown as a separate element in FIG. 4, the aperture support structure can comprise heat treated or adhesively treated portions of bodyside liner 22 of substrate 18 as disclosed earlier. Further, the depth and length of exudate containment panel 31 of the second embodiment can substantially correspond to the values disclosed earlier in the first embodiment of the invention.

The structure of the second embodiment of exudate panel 31 is better shown in FIG. 6. As seen there, exudate panel 31 includes front edges 42. Front edges 42 are folded inwardly defining front wall 43. Ends 54 of exudate panel 31 preferably are crimped and sealed when forming the panel to provide impermeable end seals that retain exudates therein. Sealing can be accomplished by crimping, adhesive bonding, ultrasonic bonding or other methods well known to one having ordinary skill in the art.

FIG. 7 shows a cross section of exudate panel 31 of FIGS. 5 and 6. Instead of having an indentation 40, exudate panel 31 has a greater number of lesser amplitude linear cross-direction undulations 46 extending across the entire width and length of the exudate panel 31. Undulations 46 are substantially perpendicular to longitudinal axis 20. Undulations 46 allow rear wall 44 to change its effective length in response to changes in the position of the personal care article or the amount of exudates in containment receptacle 30. Undulations 46 can comprise, for example, creping formed in exudate panel 31 during manufacturing. The creping expands the potential effective length of rear wall 44 when the personal care article is bent as in FIG. 4. Undulations 46 preferably extend about the entire rectangular U-shaped exudate panel 31 as shown in FIG. 6.

Exudate panel 31 can be formed of thermoplastic materials such as vinyl, polypropylene and polyethylene. Exudate panel 31 preferably has a clothlike feel, especially on its outer surface. Exudate panel 31 can also be formed from sheets of material similar to the material of outer cover 50 described herein.

Front wall 43 is secured to substrate 18, for example, by lines 52 of adhesive extending along the length of exudate panel 31 outwardly from front edges 42. Placing adhesive on ends 54 assists in securing exudate panel 31 to substrate 18, thus defining exudate containment receptacle 30. Adhesive lines 52 and adhesive placed on ends 54 of exudate panel 31 provide a liquid-tight seal for exudate containment in exudate containment receptacle 30.

In operation, undulations 46 can expand rear wall 44 along its entire length, and front wall 43 in areas away from adhesive lines 52. Further, the in-folding of front wall 43 provides for additional volumetric capacity in exudate containment receptacle 30. Thus, for a given plan view outline of exudate containment receptacle 30, the volumetric capacity of receptacle 30 is greater than that set forth for the single indentation 40 in the first embodiment, and enables containment receptacle 30 to receive and retain larger quantities of body exudates.

The embodiments of FIGS. 1–4 and the embodiment of FIGS. 5–7 can be modified to include an outer cover. FIG.

8A is a cross section view of FIG. 5 having bodyside liner 22 no longer cut-away, and without an outer cover. Only bodyside liner 22 of substrate 18 and exudate panel 31 are shown. Outer cover 50 is not necessary where bodyside liner 22 and exudate containment receptacle 30 have enough structural strength to provide a reliable personal care article 8.

Figure 8A:
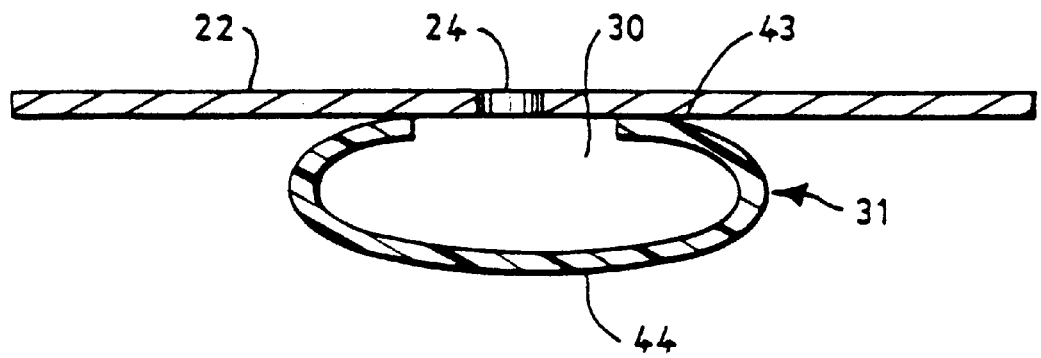
FIG. 8A shows a cross-section view of the personal care article taken at 8A—8A of FIG. 5 with the bodyside liner no longer cut-away.
Figure 8B:
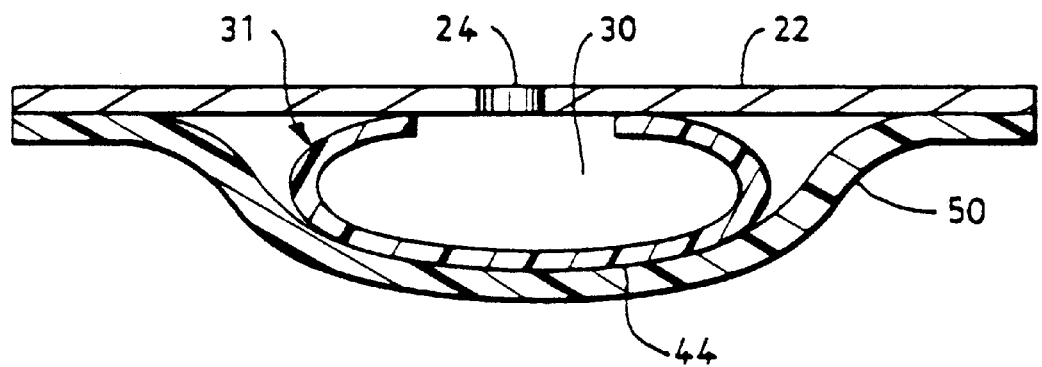
FIG. 8B shows a cross-section view as in FIG. 8A, and incorporating an outer cover.

Optionally, outer cover 50 can be secured to bodyside liner 22 of substrate 18 and rear wall 44 of exudate panel 31 as shown in FIG. 8B. This arrangement creates a product that appears more like a conventional personal care article 8 to the eye of a potential user. In embodiments utilizing outer cover 50, the outer cover preferably is formed from a material which is substantially impermeable to liquid. A typical outer cover 50 may be manufactured from a thin plastic film or other flexible liquid-impermeable material. For example, outer cover 50 can be formed from a polyethylene film. When it is desirable that outer cover 50 have a more clothlike feeling, it may comprise, for example, a polypropylene film having thermally or otherwise laminated thereto a spunbonded web of polyolefin fibers. Further, outer cover 50 can be formed of a woven or nonwoven fibrous web which has been totally or partially constructed or treated to impart a desired level of liquid impermeability to selected regions, or to all regions. Still further, outer cover 50 may optionally be composed of a micro-porous material which permits vapors to escape through outer cover 50 while preventing liquid exudates from passing through the outer cover.

Outer cover 50 is typically secured to the outer surface of bodyside liner 22 and may or may not be secured to the outer surface of exudate panel 31. Securement to exudate panel 31 is generally not continuous, and preferably is at selected spaced locations. In the region of exudate panel 31, outer cover 50 can be pleated or loose during securement. Such securement allows exudate panel 31 to increase its effective length during usage. The use of adhesives, ultrasonic bonding, sewing, and other known methods of securing outer cover 50 to bodyside liner 22 and exudate panel 31 are contemplated herein.

Figure 9:
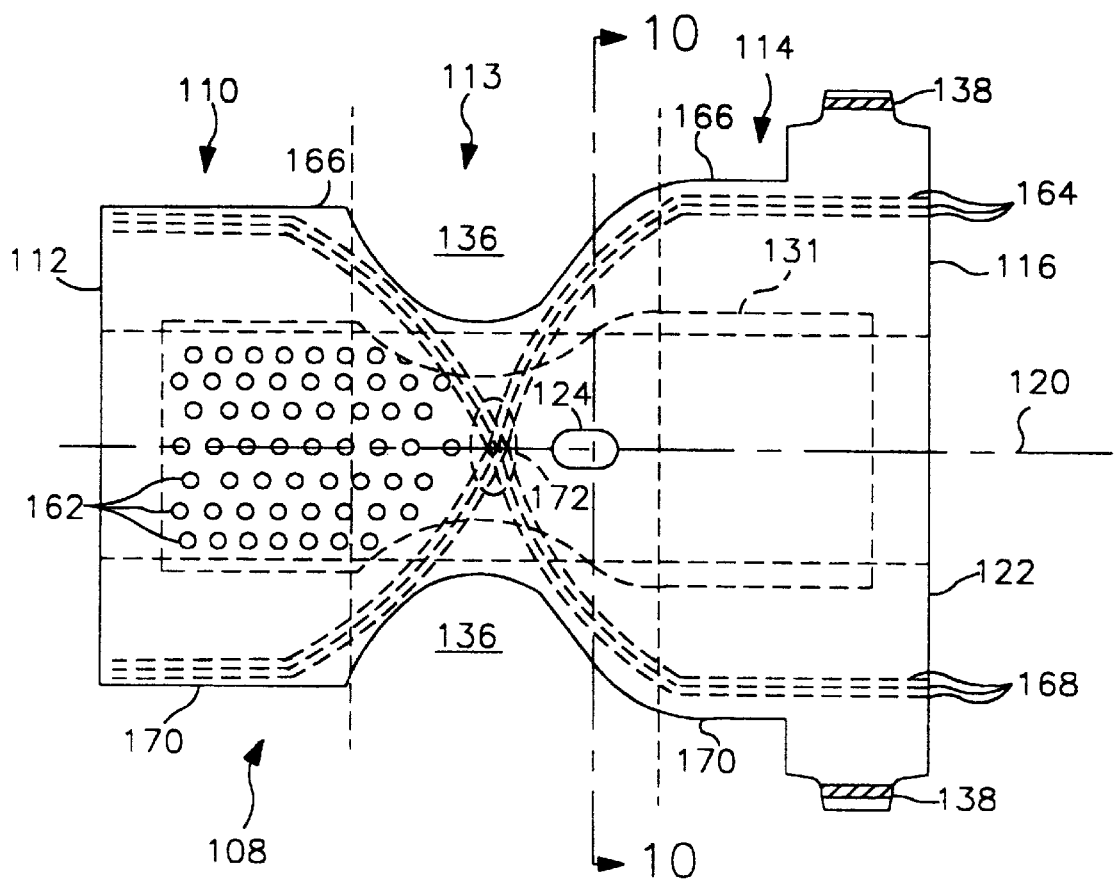
FIG. 9 shows a top view of a third embodiment of personal care articles of the invention.

FIG. 9 illustrates a third embodiment of the invention. Like numerals represent elements like those described in the earlier embodiments, with addition of the prefix "1". Dashed lines indicate elements located below the surface of bodyside liner layer 122. Personal care article 108, as shown in FIG. 9, includes a front portion 110 having a front edge 112, a crotch portion 113, and a rear portion 114 having a rear edge 116. A longitudinal axis 120, centered across the width of personal care article 108, extends through front portion 110, crotch portion 113, and rear portion 114. Personal care article 108 includes leg cut-outs 136 and fasteners 138 for securement to the body of a user.

Dashed outline 131 represents exudate panel 131 in FIG. 9. Personal care article 108 includes a substrate 118 having a bodyside liner layer 122, an aperture 124, and outer layer 176. In some embodiments substrate 118 includes comfort stretch layer 174. An aperture support structure is defined by elastomeric elements 164, 168. Aperture 124 allows fecal material to pass through substrate 118 and into a containment receptacle located between the substrate and exudate panel 131 (See FIGS. 12 and 13). Front portion 110 and crotch portion 113 include a plurality of apertures 162, which allow urine to pass through substrate 118.

Elastomeric elements 164, in combination, comprise a first support band of the aperture support structure. Elastomeric elements 164 extend from rear edge 116 in a path along outside edge 166 of personal care article 108. Elastomeric elements 164 extend inwardly at crotch portion 113. Elastomeric elements 168, in combination, comprise a second support band. Elastomeric elements 168 extend from rear edge 116 along opposing outside edge 170 of personal care article 108. Elastomeric elements 168 extend inwardly at crotch portion 113. Elastomeric elements 164 effectively meet elastomeric elements 168 in crotch portion 113 at a cooperative location 172 frontward of aperture 124. Cooperative location 172 is proximate the perineum of the body of a user when personal care article 108 is placed thereon. After effectively meeting, elastomeric elements 164, 168 cross each other, and extend therefrom in outwardly and frontwardly disposed curves toward front edge 112 of front portion 110 of personal care article 108. Thus elastomeric elements 164 traverse a path adjacent outside edge 166 in rear portion 114 and adjacent outside edge 170 in front portion 110 of personal care article 108. Likewise elastomeric elements 168 traverse a path adjacent outside edge 170 in rear portion 114 and adjacent outside edge 166 in front portion 110 of personal care article 108. Other arrangements are contemplated. For example, elastomeric elements 164, 168 can meet at cooperative location 172 and then follow a path in the front portion outwardly adjacent the same outside edge the respective elastomeric elements were adjacent in rear portion 114 of the personal care article. Further, elastomeric elements 164, 168 need not extend to front edge 112 or rear edge 116 of personal care article 108 for the embodiment to function properly.

Elastomeric elements 164, 168 position and seat aperture 124 in the gluteal fold between the buttocks of a user at or adjacent, and in alignment with the anus, to receive fecal material. The proper mounting location for aperture 124 is greatly assisted by elastomeric elements 164, 168, meeting each other, and respectively crossing laterally at cooperative location 172 whereby the strategic placement of elastomeric elements 164, 168, cooperates with respective body structure of the user to stabilize the personal care article on the body of the user, against side-to-side movement of the personal care article with respect to the body of the user. The limited elongation of elastomeric elements 164, 168, in combination with strategic placements thereof, including crossing cooperative location 172, assists in stabilizing aperture 124 both laterally and longitudinally.

When personal care article 108 is placed on the body of a user, elastomeric elements 164, 168 are proximate the perineum of the body of the user and maintain a position relative thereto. Thus aperture 124 is centered adjacent the anus of the body of the user due to the designed spacing between the aperture and elastomeric elements 164, 168 at cooperative location 172 and is laterally and longitudinally stabilized there by elastomeric elements 164, 168.

Substrate 118, having greater extensibility per unit of force than elastomeric elements 164, 168, retractively expands to cover the body of the user in a skin tight fashion. Thus substrate 118 becomes the equivalent of a second skin layer on the body of the user. Fecal material is then received through aperture 124 adjacent the anus of the user. Since fecal material passes directly through aperture 124, less fecal material contacts the skin of the user. Therefore comfort and cleanliness of the user are enhanced by personal care article 108.

While elastomeric elements 164, 168 are shown as groups of three elastomeric elements, other numbers of elements greater or less than three can be utilized. Elastomeric elements 164, 168 can comprise LYCRA elastomeric thread available from Dupont located in Wilmington, Del.

Other aperture support structures, such as those disclosed earlier in the application may be utilized to provide the characteristics of lines of force. For example, the support bands can comprise lines of force generated by an adhesive or by heat treating bodyside liner layer 122.

Figure 10:
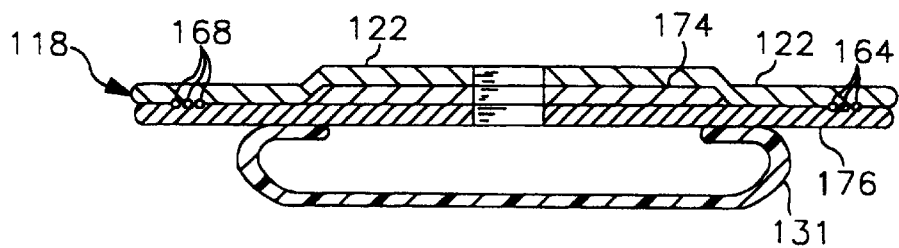
FIG. 10 shows a cross-section view of the personal care article taken at 10—10 of FIG. 9.

Elastomeric elements 164, 168 preferably are located between bodyside liner layer 122 and outer layer 176 as shown in FIG. 10. Where comfort stretch layer 174 is present, elastomeric elements can be located between comfort stretch layer 174 and bodyside liner layer 122. Elastomeric elements 164, 168 can also be located between comfort stretch layer 174 and outer layer 176. In any event, all the elastomeric elements are preferably located on a single side of comfort stretch layer 174. Elastomeric elements 164, 168 can be intermittently secured to substrate 118 or secured along the entirety of the respective paths of traverse along the substrate.

Figure 11:
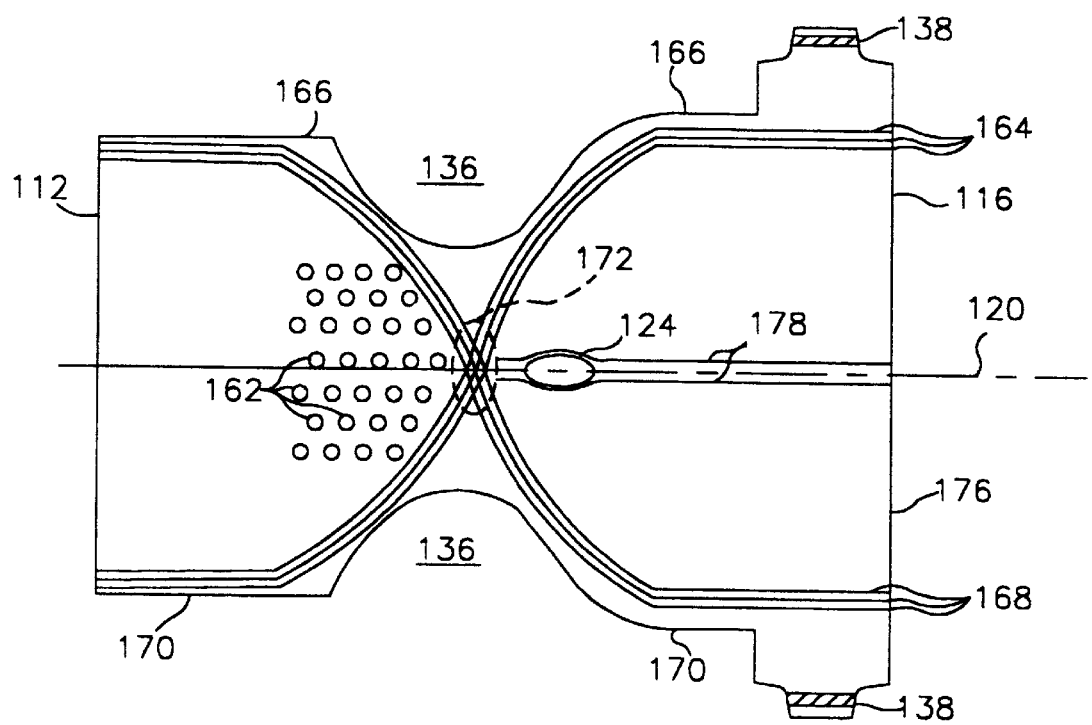
FIG. 11 shows a top view of a fourth embodiment of personal care articles of the invention with the bodyside liner layer removed.

While FIGS. 9–11 show the support bands being secured at preferred paths between bodyside liner layer 122 and outer layer 176, other arrangements are contemplated. For example, the support bands comprising elastomeric elements 164, 168 in FIG. 9 can be secured to the outer surface of bodyside liner layer 122 or to the outer surface of outer layer 176. Elastomeric elements 164, 168 can be secured continuously or at intermittent locations along their length.

Comfort stretch layer 174 is illustrated by dashed lines in FIG. 9 and shown in the cross sectional view in FIG. 10. Comfort stretch layer 174 is deposited between bodyside liner layer 122 and outer layer 176. Thus opposing sides of comfort stretch layer 174 are in surface-to-surface relationship with respective surfaces of bodyside liner layer 122 and outer layer 176. Substrate 118 comprises the combination of bodyside liner layer 122, outer layer 176, and comfort stretch layer 124. Elastomeric elements 164, 168 generally are also located between bodyside liner layer 122 and outer layer 176.

Comfort stretch layer 174 preferably comprises an elastomeric, hot melt, pressure-sensitive adhesive. The comfort stretch layer has a stretch-to-stop extensibility of at least 300% from the rest dimensions in both the "x" and "y" directions. The "y" direction, of course, represents the direction of longitudinal axis 120 and the "x" axis represents the direction transverse to the longitudinal axis. Comfort stretch layer 174 comprises a stress/strain relationship of 0.75 grams average stress per 1.0% elongation per inch width. Comfort stretch layer 174 generally is an impermeable barrier preventing passage of liquids therethrough. Comfort stretch layer 174 can comprise a unitary sheet of material. The unitary sheet or film of material preferably has a thickness from about 0.001 inch to about 0.05 inch. Such elastomeric, hot melt, pressure sensitive, adhesives are available from Findley Adhesives, Inc., Wauwatosa, Wis., under the trade designation Findley H2503 and H2504. U.S. patent application Ser. No. 08/555,011, filed Nov. 9, 1995, the disclosure of which is hereby incorporated by reference in its entirety, describes such adhesives for use in a personal care article. Other products, such as KRATON-G, or the like, can be used in comfort stretch layer 174.

As shown in FIG. 9, comfort stretch layer 174 can have a width of about one third the width of personal care article 108. The width of personal care article 108 is measured at the widest location across the personal care article, excluding fasteners 138. Thus comfort stretch layer 174 can have a width of about 4 inches. Comfort stretch layer 174 is generally symmetric with respect to longitudinal axis 120. In some embodiments, comfort stretch layer 174 can extend other distances across personal care article 108. For example, comfort stretch layer 174 can extend substantially the entire width and length of personal care article 108.

Bodyside liner layer 122 and outer layer 176 of FIG. 10 can comprise materials described in earlier embodiments describing bodyside liner 22. Bodyside liner layer 122 and outer layer 176 preferably each have stretch-to-stop extensibility in both the "x" and "y" directions of from about 20% to about 200% of the respective rest dimensions.

At least outer layer 176 is generally impermeable. Bodyside liner layer 122 can also be impermeable. Bodyside liner layer 122 preferably is not wettable. Thus bodyside liner layer does not wick fluid contacting thereon. Therefore more exudates pass through aperture 124 and plurality of apertures 162, respectively, because bodyside liner layer 122 does not wick away exudates.

Likewise, fasteners 138, front waistband (not shown in FIGS. 9 and 11), and rear waistband (not shown in FIGS. 9 and 11) can be similar to like elements described in earlier embodiments of the invention.

Aperture 124 has an oval shape in FIG. 9. Aperture 124 can have a wide variety of shapes and dimensions such as those described earlier with respect to the aperture of FIGS. 1, 4, and 5. Aperture 124 is positioned and seated in the gluteal fold adjacent, and in alignment with, the anus to receive fecal material.

Plural apertures 162 are located in front portion 110 and crotch portion 113 of personal care article 108. Any number from one to a multiplicity of apertures can be utilized. The size of plural apertures 162 can be varied depending, for example, on the number of apertures in the embodiment.

Plural apertures 162, allowing urine to pass therethrough, can have any desired shape. While circular shapes are disclosed, rectangular, elliptical, and slit shapes can, for example, be utilized. The only requirement of the shapes is that they permit urine to effectively flow into the containment receptacle.

The embodiment of FIGS. 9 and 10 thus comprises a final product having at least about 30% stretch-to-stop extensibility in the "y" direction along longitudinal axis 120 of the personal care article taken with respect to the length of the article at rest. The final product includes substrate 118 comprising bodyside liner layer 122, comfort stretch layer 174, and outer layer 176. Support bands preferably comprising elastomeric elements 164, 168 are, of course, also a part of the final product. The amount of stretch of the overall personal care article can vary depending, for example, on whether absorbent pad 180 is utilized, and whether such pad is secured to exudate panel 131.

Depending on the amount of stretch in comfort stretch layer 174 when the comfort stretch layer is secured to substrate 118, the amount of stretch in elastomeric elements 164, 168, when secured to substrate 118, and other factors, the overall stretch-to-stop length of personal care article 108 can be at least about 40% greater in length than the length at rest in the "y" direction. In other embodiments, the overall stretch-to-stop length for article 108 can be about 50% greater than the length of the article at rest. In other embodiments, the overall stretch-to-stop length for article 108 can be 60% greater than the length of the article at rest. In other embodiments, the overall stretch-to-stop length for article 108 can be about 70% greater than the length of the personal care article at rest. An overall stretch-to-stop length for article 108 preferably is at least about 80% greater, and more preferably at least about 90% greater, than the length of the article at rest.

In use, personal care article 108 conforms to the anatomy of the wearer. The front of cooperative location 172 where elastomeric elements 164, 168 cross over tends to seat itself on the perineum which acts as an effective locator on the body of the user. In this way aperture 124 and the anus of the body of a user are registered and aligned with each other to allow transfer of exudates.

FIG. 11 shows a modified embodiment of FIG. 9 having bodyside liner layer 122 temporarily removed to better view the elements. FIG. 11 comprises essentially the same invention as shown in FIG. 9 except for an additional support element in the support structure. Further, the embodiment of FIG. 11 does not necessarily include comfort stretch layer 174. In this embodiment, elastomeric elements 178 provide a third support element extending at least from aperture 124 toward rear portion 114. Elements 178 optionally extend about the perimeter of aperture 124, optionally to cooperative location 172. Elastomeric elements 178 can follow elastomeric elements 164, 168 frontwardly into front portion and thus extend along the full length of personal care article 108. The third support element assists in seating and positioning aperture 124 in the gluteal fold between the buttocks of the user at or adjacent the anus, to receive fecal material from the user. Thus, the embodiment of FIG. 11 functions like the embodiment of FIGS. 9 and 10, except for third elastomeric elements 178 comprising a line of force positioned in the gluteal fold of the body of a user. Therefore personal care article 108 compensates for less stretch of the skin or substrate 118 due to the absence of comfort stretch layer 174.

Figure 12:
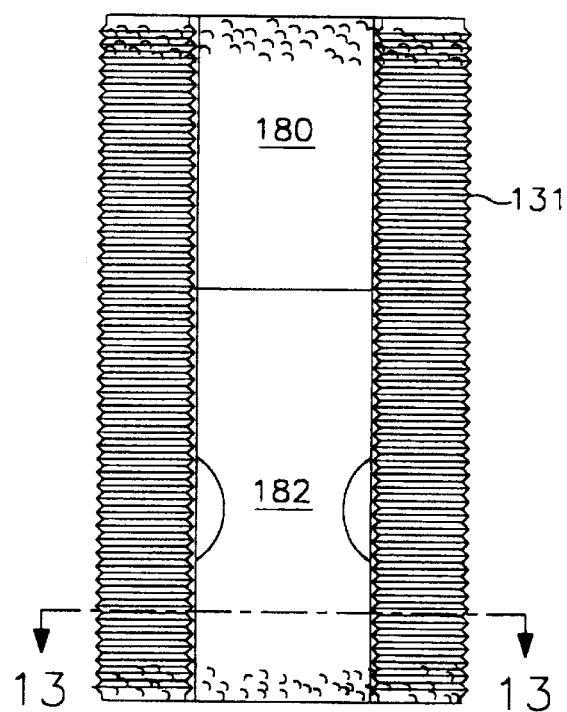
FIG. 12 shows an exudate panel containing an absorbent pad having a surge layer.
Figure 14:
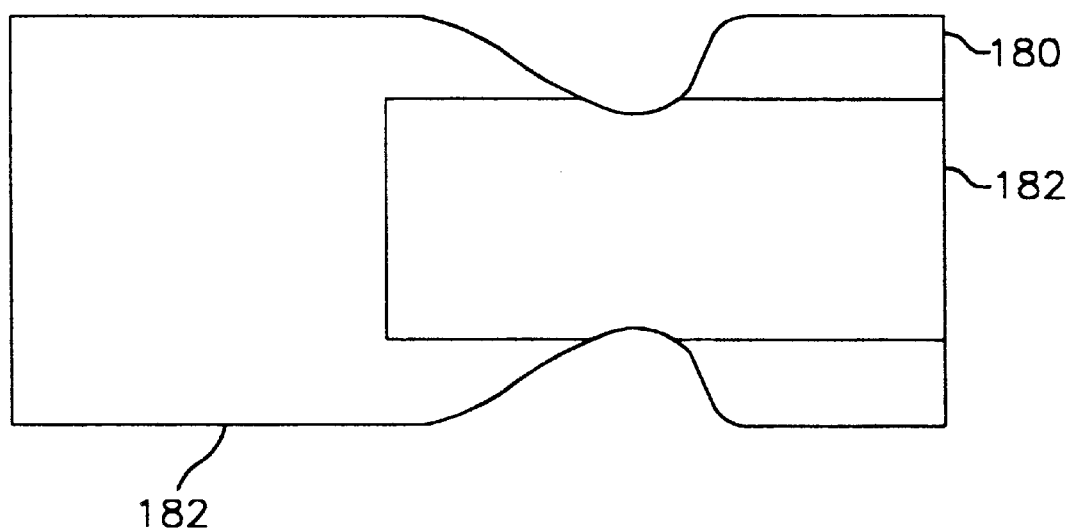
FIG. 14 shows the absorbent pad including a surge layer for use in the exudate panel of FIG. 12.

FIG. 12 shows exudate panel 131 containing an absorbent pad 180 (see FIG. 14). Exudate panel 131 can be formed of thermoplastic materials such as vinyl, polypropylene or polyethylene. Exudate panel 131 preferably has a clothlike feel, especially on its outer surface. Exudate panel 131 can also be formed from sheets of material similar to the material of outer cover 50 described earlier. Exudate panel 131 is secured to substrate 118 by adhesives or the like, as described earlier, to form a personal care article 108 including a containment receptacle.

Figure 13:
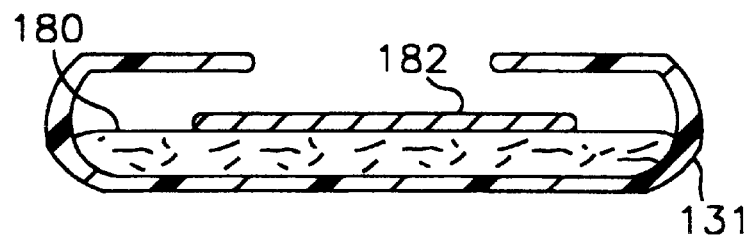
FIG. 13 shows a cross-section view taken at 13—13 of FIG. 12 showing the relationship between the exudate panel, absorbent pad, and surge layer.

FIG. 13 shows a cross-section view of exudate panel 131, absorbent pad 180, and surge layer 182 taken at 13—13 of FIG. 12. Absorbent pad 180 can be loosely placed, or adhesively secured to exudate panel 131. Surge layer 182 is secured to absorbent pad 180. Thus FIG. 12 shows the arrangement of the elements before securement of the combination of exudate panel 131, absorbent pad 180, and surge layer 182, to substrate 118. Securement can be made by adhesive or the like.

Securement of exudate panel 131 to substrate 118 forms the containment receptacle for personal care article 108. As described earlier, elastomeric elements 164, 168 have less extensibility than substrate 118. Thus elastomeric elements 164, 168 form support bands defining lines of force positioning and seating personal care article 108 on the body of the user.

Absorbent pad 180, shown in FIG. 14, can comprise a matrix of hydrophilic fibers, such as a web of cellulosic fluff. In some embodiments, the matrix can be combined with a high-absorbency material commonly known as superabsorbent material. In a particular embodiment, absorbent pad 180 comprises a mixture of superabsorbent hydrogel-forming particles and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent pad 180.

Alternatively, absorbent pad 180 may comprise a laminate of fibrous webs and superabsorbent material or other suitable means for maintaining a superabsorbent material in a localized area.

The absorbent pad 180 may have any of a number of shapes. For example, the absorbent pad may be rectangular, I-shaped or T-shaped. As shown in FIG. 14, it is generally preferred that absorbent pad 180 be narrower in crotch portion 113 than rear portion 114 or front portion 110.

The high-absorbency material in the absorbent pad 180 can be selected from natural, synthetic and modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

As shown in FIGS. 13 and 14, absorbent pad 180 can include a surge layer 182. Surge layer 182 assists in containing a sudden, large amount of exudates. Thus surge layer 182 improves performance of personal care article 108.

Surge layer 182 can comprise materials set forth in U.S. patent application Ser. No. 206,986 by C. Ellis and D. Bishop, entitled, "Fibrous Nonwoven Web Surge Layer for Personal Care Absorbent Articles and the Like", filed Mar. 4, 1994; refiled Feb. 9, 1995 and issued as U.S. Pat. No. 5,486,166 and U.S. patent application Ser. No. 206,069 by C. Ellis and R. Everett, entitled, "Improved Surge Management Fibrous Nonwoven Web for Personal Care Absorbent Articles and the Like", filed Mar. 4, 1994 refiled Feb. 9, 1995 and issued as U.S. Pat. No. 5,490,846, the disclosures of which are herein incorporated by reference. Further, other surge layer materials known in the art can also be utilized.

In the embodiments of FIGS. 9–14, personal care article 108, including substrate 118 and exudate panel 131, can utilize an outer cover, as shown in FIG. 8B, to create a product that appears more like a conventional personal care article to the eye of a potential user.

In all of the embodiments described, personal care article 8,108 preferably is free from containment flaps. As indicated, aperture 24, 124 is located adjacent the anus when in use, and bodyside liner 22, and bodyside liner layer 122 are generally impermeable to liquid. Fecal material generally passes directly from the anus through aperture 24, 124 and into exudate containment receptacle 30. Small amounts of fecal material may collect near anus 56. However, because of the alignment between anus 56 and aperture 24, 124, the amount of fecal material collecting is so small that fecal material generally does not spread far from the anus. Thus personal care article 8, 108 receives and retains exudates without any need for containment flaps. Optionally, containment flaps can be provided to reassure the wearer of the ability of the personal care article to contain exudates.

Personal care article 8, 108 generally does not require leg cuffs, but may require reinforcing perimeter seams or extra material for strength and gasketing. In the embodiment of FIGS. 9–11, the aperture support structure tends to be adjacent the outer edge of personal care article 108 and somewhat function as leg cuffs. Substrate 18, 118 including bodyside liner 22, or bodyside liner layer 122, respectively have enough extensibility to mount personal care article 8, 108 to the body of a user with leg cut-outs 36, 136 helping conform the article to the body.

In the embodiments of FIGS. 1–8 of the invention, aperture support structure 26, when mounted on a user, may generally follow the area of the minimum arc skin lines in the gluteal fold, and in the groin between the trunk and legs. Because the skin in those areas is so sensitive, the materials of aperture support structure 26, including support bands 26A, 26B, 26C is selected for its balance of properties of both (a) limiting stretch of substrate 18 along structure 26 and (b) being soft and supple, and thus gentle on the skin of the user.

As used herein and in the claims that follow, the phrase "thermoformed depth" refers to the depth of the exudate panel when first formed. "Thermoformed" is meant to include both highly flexible plastic materials and somewhat rigid plastic materials and includes both exudate panels formed by a thermoforming process and exudate panels formed by other processes. The phrase is not limited to exudate panels formed by what are conventionally known as thermoforming processes.

As used herein and in the claims that follow, the phrase "personal care article" is meant to include adult incontinence articles, feminine hygiene products, articles storing urine and/or fecal material that have no absorbent material, and absorbent articles storing urine and/or fecal material that have absorbent material.

As used herein and in the claims that follow, the term "layer" is meant to include an element comprising a single sheet or film of unitary material, a composite of multiple layers of material, or other known arrangements comprising a sheet of material, or the like.

Different personal care article sizes are required for infants, adults, or other users of the product.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A personal care article for receiving exudates, said personal care article having a front edge and a rear edge, and a length and a width, and comprising:
    (a) a substrate having an overall surface area thereof, said substrate including a generally resiliently extensible liquid impermeable layer configured in said personal care article to be positioned toward the body of a wearer;
    (b) at least one of an exudate panel or an outer cover, together with said substrate, forming an exudate receptacle between said substrate and said at least one exudate panel or outer cover;
    (c) at least one aperture in said substrate, extending through said generally resilient extensible layer, the size of the aperture generally corresponding to the size of the anal opening of such a wearer for whom said personal care article is suitably sized; and
    (d) aperture support structure having limited resilient extensibility, substantially less than the resilient extensibility of said generally resiliently extensible layer, said aperture support structure extending along one or more paths on said substrate, thereby passing adjacent the at least one aperture, and effectively extending sufficiently far away from the at least one aperture so as to limit extensibility of said substrate along the one or more paths passing adjacent the at least one aperture, thereby to limit movement of the at least one aperture with respect to the remainder of said substrate, the limited extensibility of the general resilient properties of said generally resiliently extensible layer generally conforming said personal care article to the body of the wearer, including urging the aperture into the gluteal fold for alignment with the anal opening of the wearer, said aperture support structure limiting movement of the aperture with respect to the remainder of said substrate, and thereby restricting movement of the aperture with respect to the anal opening of the wearer, the combination of the extensibility of the generally resiliently extensible layer, and the limiting extensibility of said aperture support structure supporting the aperture into generally intimate relationship with the body of the wearer at or adjacent the anal opening, the aperture thus being positioned for passage of exudate material, directly from the anal opening of the wearer, through the aperture at or adjacent the anal opening, and into the exudate receptacle.

2. The personal care article as in claim 1, said exudate panel secured to said substrate and defining the exudate receptacle between said exudate panel and said substrate.

3. A personal care article as in claim 2, the length comprising a first length, said exudate panel having a second length substantially aligned with the first length, a thermoformed depth, and an indentation extending across at least the second length of said exudate panel and inwardly toward said substrate at least about 30% of the thermoformed depth of said receptacle such that the effective second length of said exudate panel increases when said containment receptacle is bent or filled with exudates.

4. A personal care article as in claim 2, the length comprising a first length, said exudate panel having a second length substantially aligned with the first length, and having undulations extending across at least the second length of said exudate panel such that the effective second length of at least said exudate panel increases when said containment receptacle is bent or filled with exudates.

5. The personal care article as in claim 1, the limited resilient extensibility of said aperture support structure comprising extensibility of about 1% to about 10% of the rest length thereof.

6. The personal care article as in claim 1, the length comprising a first length, said personal care article including an exudate panel secured over a second partial length of said substrate, said aperture support structure extending substantially the full amount of the second partial length of said substrate.

7. The personal care article as in claim 1, said generally resiliently extensible layer comprising an elastomeric material extensible in both "x" and "y" directions.

8. The personal care article as in claim 5, said generally resiliently extensible layer comprising an elastomeric material extensible in both "x" and "y" directions, and having a stretch-to-stop extensibility of about 20% to about 200% of the length at rest in both directions.

9. The personal care article as in claim 1, said aperture support structure comprising portions of said generally resiliently extensible layer treated with adhesive to thereby reduce extensibility.

10. The personal care article as in claim 1, said aperture support structure comprising a separate piece of material, said separate piece of material being secured to said generally resiliently extensible layer.

11. The personal care article as in claim 1, said aperture support structure comprising portions of said generally resiliently extensible layer treated with heat to thereby reduce extensibility along the one or more paths.

12. The personal care article as in claim 1, said exudate panel secured to said substrate and defining front and rear containment receptacles having depths between said exudate panel and said substrate, said exudate panel being positioned over said aperture such that said rear containment receptacle receives exudates through said aperture.

13. A personal care article for receiving exudates, said personal care article having a front portion including a front edge, and a rear portion including a rear edge, said personal care article further comprising:
  (a) a substrate, including a generally resiliently extensible liquid impermeable layer configured in said personal care article to be positioned toward the body of a wearer;
  (b) at least one of an exudate panel or an outer cover, together with said substrate, forming an exudate receptacle between said substrate and said at least one exudate panel or outer cover;
  (c) at least one aperture in said substrate, extending through said generally resilient extensible layer, the size of the aperture generally corresponding to the size of the anal opening of such a wearer for whom said personal care article is suitably sized;
  (d) aperture support structure, including at least one support band having limited resilient extensibility, substantially less than the resilient extensibility of said generally resiliently extensible layer, said at least one support band extending along one or more paths from said at least one aperture to said front edge, thereby to limit movement of the at least one aperture with respect to the remainder of said substrate, the limited extensibility of the general resilient properties of said generally resiliently extensible layer generally conforming said personal care article to the body of the wearer, including urging the aperture into the gluteal fold for alignment with the anal opening of the wearer, said aperture support structure limiting movement of the aperture with respect to the remainder of said substrate, and thereby restricting movement of the aperture with respect to the anal opening of the wearer, the aperture thus being positioned in alignment with the anal opening for passage of exudate material, from the anal opening of the wearer, through the aperture, and into the exudate receptacle.

14. The personal care article as in claim 13, said personal care article having a longitudinal axis extending between said front portion and said rear portion along a length of said personal care article, said longitudinal axis being centered across a width of said personal care article, a second support band of said aperture support structure extending from said at least one aperture to said front edge, said first and second support bands of said aperture support structure each forming an angle of between about 10 degrees and about 40 degrees with respect to said longitudinal axis.

15. A personal care article as in claim 14, said first and second support bands defining a space therebetween, and including a liquid transfer structure in the space between said first and second support bands, said liquid transfer structure allowing body exudate liquids to pass therethrough and into a containment receptacle.

16. A personal care article as in claim 15, a third support band of said aperture support structure extending from said aperture to said rear edge.

17. The personal care article as in claim 15, said liquid transfer structure comprising a portion of a bodyside liner of said substrate treated with surfactant to enable urine to pass therethrough.

18. The personal care article as in claim 13, said aperture support structure effectively surrounding said aperture in close proximity to said aperture.

19. A personal care article as in claim 13, said aperture support structure extending a length of said personal care article.

20. The personal care article as in claim 13, including an exudate panel secured to said substrate and defining front and rear containment receptacles between said exudate panel and said substrate, said exudate panel being positioned over said aperture such that said rear containment receptacle receives fecal exudates from the anal opening through said aperture.

21. A personal care article as in claim 20, said front and rear containment receptacles being connected by at least one passageway allowing the transfer of exudates therebetween.

22. The personal care article as in claim 13, the limited resilient extensibility of said aperture support structure comprising extensibility of about 1% to about 10% of the rest length thereof, said generally resiliently extensible layer of said substrate comprising an elastomeric material extensible in both "x" and "y" directions, and having a stretch-to-stop extensibility of about 20% to about 200% of the length at rest in both directions.

23. A personal care article for receiving body exudates, said personal care article having a front portion and a rear portion, and further comprising:
  (a) an impermeable bodyside liner;
  (b) liquid transfer structure in the front portion of said personal care article, said liquid transfer structure comprising permeable sheet material, permeable to passage of liquid body exudates from a first side of said sheet material through said sheet material to a second side thereof; and
  (c) an exudate containment panel secured to said bodyside liner and at least in part defining an exudate containment receptacle,
  (d) at least one aperture in said bodyside liner for passage of exudate material from the anal opening of the wearer into the exudate containment receptacle, said exudate containment receptacle receiving and containing fecal material passing through said at least one aperture, and urine passing through said liquid transfer structure.

24. A personal care article as in claim 23, said bodyside liner permitting vapors to escape therethrough.

* * * * *

UNITED STATES PATENT AND TRADEMARK OFFICE
CERTIFICATE OF CORRECTION

PATENT NO.   : 6,132,409
DATED        : October 17, 2000
INVENTOR(S)  : Robert Eugene Vogt et al.

It is certified that error appears in the above-identified patent and that said Letters Patent is hereby corrected as shown below:

Column 1,
Line 49, delete "eptured", and substitute -- effectively captured --.

Column 9,
Line 38, delete "angled", and substitute -- angle --.

Column 12,
Line 46, delete "a", and substitute -- $\alpha$ --.

Column 23,
Line 38, after "sized;", add -- and --.

Signed and Sealed this

Eighteenth Day of December, 2001

Attest:

Attesting Officer

JAMES E. ROGAN
Director of the United States Patent and Trademark Office